(12) United States Patent
Carrier et al.

(10) Patent No.: US 11,510,908 B2
(45) Date of Patent: Nov. 29, 2022

(54) PROTEIN TRANSLATION INHIBITORS AND USES THEREOF

(71) Applicants: France Carrier, Highland, MD (US); Alexander D. MacKerell, Baltimore, MD (US); David J. Weber, Baltimore, MD (US); Wenbo Yu, Ellicott City, MD (US)

(72) Inventors: France Carrier, Highland, MD (US); Alexander D. MacKerell, Baltimore, MD (US); David J. Weber, Baltimore, MD (US); Wenbo Yu, Ellicott City, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 59 days.

(21) Appl. No.: 16/879,226

(22) Filed: May 20, 2020

(65) Prior Publication Data
US 2020/0368208 A1 Nov. 26, 2020

Related U.S. Application Data

(60) Provisional application No. 62/892,138, filed on Aug. 27, 2019, provisional application No. 62/851,704, filed on May 23, 2019.

(51) Int. Cl.
| | | |
|---|---|---|
| *A61K 31/426* | (2006.01) | |
| *A61P 35/00* | (2006.01) | |
| *A61K 31/519* | (2006.01) | |
| *A61K 31/427* | (2006.01) | |

(52) U.S. Cl.
CPC .......... *A61K 31/426* (2013.01); *A61K 31/427* (2013.01); *A61K 31/519* (2013.01); *A61P 35/00* (2018.01)

(58) Field of Classification Search
CPC .............................. A61K 31/426; A61P 35/00
See application file for complete search history.

(56) References Cited

U.S. PATENT DOCUMENTS 10,302,629 B2 * 5/2019 Carrier ................ C12N 15/113
2016/0289311 A1 * 10/2016 Carrier .................. C07K 16/00

* cited by examiner

*Primary Examiner* — Kamal A Saeed
(74) *Attorney, Agent, or Firm* — Benjamin Aaron Adler

(57) ABSTRACT

Provided herein are protein translation inhibitors and pharmaceutical compositions thereof that bind to an RNA Recognition motif in heterogeneous ribonucleoprotein A18 to inhibit binding to mRNA transcripts thereby inhibiting protein synthesis. Also provided is a method for treating a cancer by administering a pharmaceutically acceptable amounts of at least one of the protein translation inhibitors.

14 Claims, 22 Drawing Sheets

Specification includes a Sequence Listing.

```
SEQ ID NO: 9   GCA-AUCCAGGCUGGGA--UUUCUUGAGGAAGUACAAAUAAGCUUGUUAGA
SEQ ID NO: 10  UCUGGUACAGGUGUUAU--UGUCUGUUA-AAACUA----GUCUGC------AGA
SEQ ID NO: 11  UGAGCUUGCUGUUG----UACACAGGGU-AUUCUAGA---AGCAG-------AAA
SEQ ID NO: 12  UAGUUGGCAGGUG-----UAGACUUUUU-AAGUGG------GCUUU------AGA
SEQ ID NO: 13  CCUUAUGUCAGUUG----UCUACUCUGG-AGCUU------GACUU-------GGA
SEQ ID NO: 14  UCUGUUUUAUUUG-----UUUGUUUGAA-GCUCA------GAGGG-------AGA
SEQ ID NO: 15  UA--UUUAAACUUGUAUUUUUUUAUUU--A-CAAAAUAAAUAUGAAG----A          (34-78)
(Trx)
SEQ ID NO: 16  GAUGCUaaAAGGUUGUAUUgCaUaUaUacAUAuAUAUAUAuAUAUAUAu--A         (1319-1370)
(CTLA-4)
```

FIG. 9A

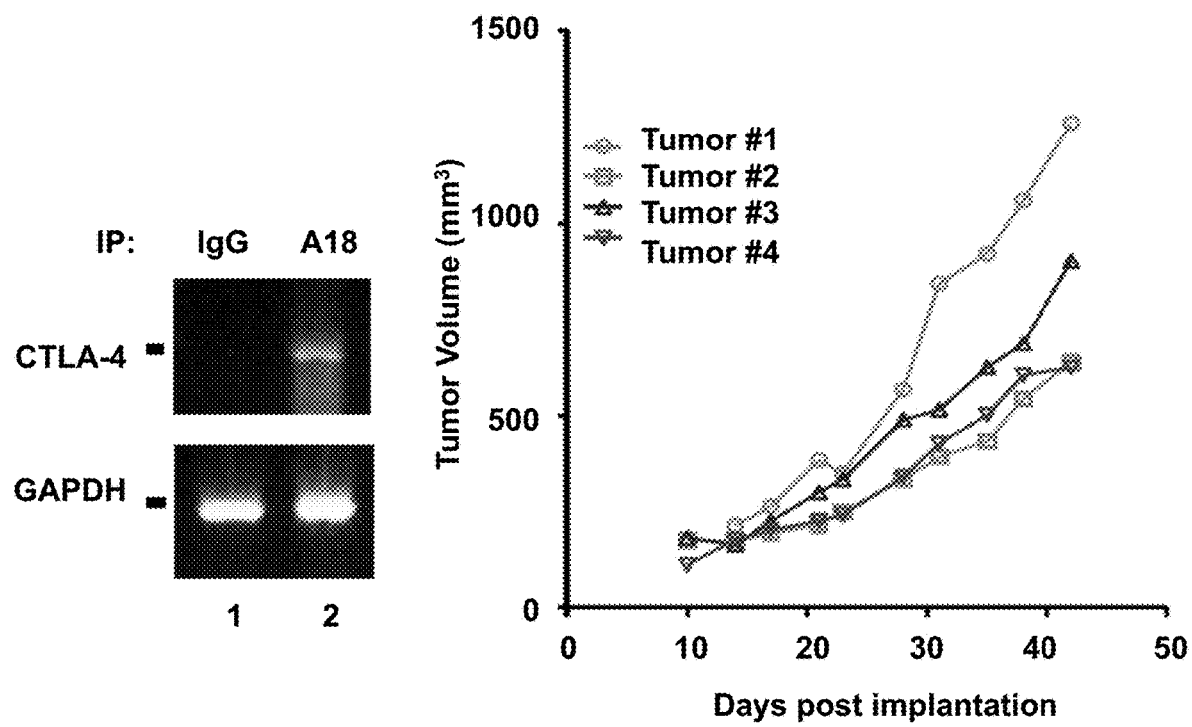
FIG. 9B
FIG. 9C
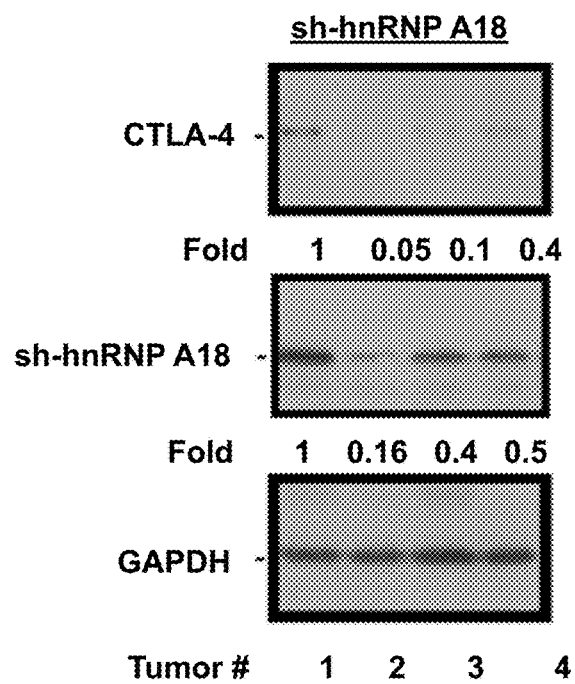
FIG. 9D

SEQUENCE LISTING

<160> NUMBER OF SEQ ID NOS: 16

<210> SEQ ID NO 1
<211> LENGTH: 51
<212> TYPE: RNA
<213> ORGANISM: Artificial Sequence
<220> FEATURE:
<223> OTHER INFORMATION: Heterogenous ribonucleoprotein A18 motif 1
      probe sequence
<220> FEATURE:
<221> NAME/KEY: modified_base
<222> LOCATION: 51
<223> OTHER INFORMATION: Adenosine at position 51 is modified with
      T-Fluorescein

<400> SEQUENCE: 1
gcagauccag ggugggauuu ucuugaggaa guuacaaaua agcuuguuac a            51

<210> SEQ ID NO 2
<211> LENGTH: 51
<212> TYPE: RNA
<213> ORGANISM: Artificial Sequence
<220> FEATURE:
<223> OTHER INFORMATION: Heterogenous ribonucleoprotein A18 motif 1
      probe sequence
<220> FEATURE:
<221> NAME/KEY: modified_base
<222> LOCATION: 51
<223> OTHER INFORMATION: Adenosine at position 51 is modified with
      biotin

<400> SEQUENCE: 2
gcagauccag ggugggauuu ucuugaggaa guuacaaaua agcuuguuac a            51

<210> SEQ ID NO 3
<211> LENGTH: 51
<212> TYPE: RNA
<213> ORGANISM: Artificial Sequence
<220> FEATURE:
<223> OTHER INFORMATION: Iron responsive element probe sequence
<220> FEATURE:
<221> NAME/KEY: modified_base
<222> LOCATION: 51
<223> OTHER INFORMATION: Cytosine at position 51 is modified with biotin

<400> SEQUENCE: 3
uccugcuuca acagugcuug gacggaacuc cugcuucaac agugcuugga c            51

<210> SEQ ID NO 4
<211> LENGTH: 28
<212> TYPE: RNA
<213> ORGANISM: Artificial Sequence
<220> FEATURE:
<223> OTHER INFORMATION: Iron responsive element probe sequence
<220> FEATURE:
<221> NAME/KEY: modified_base
<222> LOCATION: 28
<223> OTHER INFORMATION: Cytosine at position 28 is modified with biotin

<400> SEQUENCE: 4
uccugcuuca acagugcuug gacggaac                                     28

<210> SEQ ID NO 5
<211> LENGTH: 24
<212> TYPE: DNA
<213> ORGANISM: Artificial Sequence
<220> FEATURE:
<223> OTHER INFORMATION: Forward primer for cytotoxic T-lymphocyte-
      associated protein-4

<400> SEQUENCE: 5
acatcaagaa ggtggtgaag cagg                                        24

<210> SEQ ID NO 6
<211> LENGTH: 20
<212> TYPE: DNA
<213> ORGANISM: Artificial Sequence
<220> FEATURE:
<223> OTHER INFORMATION: Reverse primer for cytotoxic T-lymphocyte-
      associated protein-4

<400> SEQUENCE: 6
gcctcagctc ttggaaattg                                             20

<210> SEQ ID NO 7
<211> LENGTH: 24
<212> TYPE: DNA
<213> ORGANISM: Artificial Sequence
<220> FEATURE:
<223> OTHER INFORMATION: Forward primer for Glyceraldehyde 3-phosphate
      dehydrogenase

<400> SEQUENCE: 7
acatcaagaa ggtggtgaag cagg                                        24

<210> SEQ ID NO 8
<211> LENGTH: 25
<212> TYPE: DNA
<213> ORGANISM: Artificial Sequence
<220> FEATURE:
<223> OTHER INFORMATION: Reverse primer for Glyceraldehyde 3-phosphate
      dehydrogenase

<400> SEQUENCE: 8
ccagcaagga tactgagagc aagag                                       25

<210> SEQ ID NO 9
<211> LENGTH: 49
<212> TYPE: RNA
<213> ORGANISM: Artificial Sequence
<220> FEATURE:
<223> OTHER INFORMATION: Putative heterogenous ribonucleoprotein A18
      motif 1 recognition motif sequence

<400> SEQUENCE: 9
gcaauccagg gugggauuuc uugaggaagu uacaaauaag cuuguuaca              49

<210> SEQ ID NO 10
<211> LENGTH: 43
<212> TYPE: RNA
<213> ORGANISM: Artificial Sequence
<220> FEATURE:
<223> OTHER INFORMATION: Putative heterogenous ribonucleoprotein A18
      motif 1 recognition motif sequence

<400> SEQUENCE: 10
ucugcuuaca gguguuauuu gucuguuaaa acuagucugc aga                   43

<210> SEQ ID NO 11
<211> LENGTH: 41
<212> TYPE: RNA
<213> ORGANISM: Artificial Sequence
<220> FEATURE:
<223> OTHER INFORMATION: Putative heterogenous ribonucleoprotein A18
      motif 1 recognition motif sequence

<400> SEQUENCE: 11
ugagcuugcu guuguacaca ggguauuucu agaagcagaa a                       41

<210> SEQ ID NO 12
<211> LENGTH: 39
<212> TYPE: RNA
<213> ORGANISM: Artificial Sequence
<220> FEATURE:
<223> OTHER INFORMATION: Putative heterogenous ribonucleoprotein A18
      motif 1 recognition motif sequence

<400> SEQUENCE: 12
uaguuuggca gguguagacu uuuuaaguug ggcuuuaga                          39

<210> SEQ ID NO 13
<211> LENGTH: 37
<212> TYPE: RNA
<213> ORGANISM: Artificial Sequence
<220> FEATURE:
<223> OTHER INFORMATION: Putative heterogenous ribonucleoprotein A18
      motif 1 recognition motif sequence

<400> SEQUENCE: 13
ccuuauguca guugucuacu cuggagcuug acuugga                            37

<210> SEQ ID NO 14
<211> LENGTH: 38
<212> TYPE: RNA
<213> ORGANISM: Artificial Sequence
<220> FEATURE:
<223> OTHER INFORMATION: Putative heterogenous ribonucleoprotein A18
      motif 1 recognition motif sequence

<400> SEQUENCE: 14
ucuguuuuau uuuguuuugu uugaagcuca gagggaga                           38

<210> SEQ ID NO 15
<211> LENGTH: 45
<212> TYPE: RNA
<213> ORGANISM: Unknown
<220> FEATURE:
<222> LOCATION: 34  78
<223> OTHER INFORMATION: Thioredoxin transcript sequence

<400> SEQUENCE: 15
uauuuaaacu uguauuuuuu uauuuacaaa auauaaauau gaaga                   45

<210> SEQ ID NO 16
<211> LENGTH: 51
<212> TYPE: RNA
<213> ORGANISM: Unknown
<220> FEATURE:
<222> LOCATION: 1319  1370
<223> OTHER INFORMATION: Cytotoxic T-lymphocyte-associated protein-4
      transcript sequence

<400> SEQUENCE: 16
gaugcuaaag guuguauugc auauauacau auauauauau auauauauau a            51

PROTEIN TRANSLATION INHIBITORS AND USES THEREOF

CROSS-REFERENCE TO RELATED APPLICATIONS

This non-provisional application claims benefit of priority under 35 U.S.C. § 119(e) of provisional applications U.S. Ser. No. 62/892,138, filed Aug. 27, 2019, and U.S. Ser. No. 62/851,704, filed May 23, 2019, both of which are hereby incorporated in their entireties.

GOVERNMENTAL SPONSORSHIP

This invention was made with government support under Grant Number CA177981 awarded by the National Institutes of Health. The government has certain rights in the invention.

BACKGROUND OF THE INVENTION

Field of the Invention

The present disclosure is in the technical field of cancer therapies. More particularly, the present disclosure pertains to targeting protein translation to simultaneously inhibit cancer cell progression and an immune checkpoint.

Description of the Related Art

A growing number of human diseases, including tumorigenesis, are associated with protein translation deregulation (1). Cancer cells depend on an accelerated rate of protein translation to supply essential nutrients required to sustain constant demands by actively proliferating cells. Strategies to deprive cancer cells of these nutrients are therefore attractive approaches to limit cancer proliferation. Anticancer therapies that target the protein translation regulator mammalian Target of Rapamycin (mTOR) highlight the importance of targeting protein translation to limit cancer progression. Inhibitors of the mTOR pathway have shown clear benefits in cancers such as mantle cell lymphomas, renal cell carcinoma and Tuberous Sclerosis Complex-related tumors, but have demonstrated limited efficacy in most other cancers when administered as single agents (2).

Cancer cells have to produce a number of key regulatory proteins at an accelerated rate in order to sustain the constant demand of actively proliferating cells as well as evade the cytotoxic activity of immune cells infiltrating into the tumor. Tumor cells achieve this by hijacking the post-transcriptional mechanisms to adjust to their rapidly evolving intrinsic and extracellular environments during cancer progression. RNA binding proteins (RBPs) are critical players of post-transcriptional control of gene expression and not surprisingly, their dysregulation is associated with different types of cancer. Targeting the machinery that controls protein translation or immune checkpoints are therefore attractive approaches for cancer therapy. Although major advances have been made in developing small molecule agents to target protein-protein interactions, regulation of protein-RNA interactions lag behind due to challenges associated with disordered domains in RBPs and flexibility of RNA molecules.

One of the main challenges in cancer therapy is the resistance that often ensues following an initial response to current treatments. The underlying causes of resistance vary but often result from cancer cells bypassing the targeted pathway by adopting alternative mechanisms to maintain their growth and progression. Combined chemotherapies and modalities are regularly designed to counter compensatory mechanisms and harness cancer progression from different angles, but these approaches also combine the toxicity of the different agents. Agents that could simultaneously target selected key pathways essential for cancer cell progression and survival are therefore expected to minimize toxicity and potential resistance. Cancer therapy approaches that focus on combining chemotherapy with humanized immune checkpoint antibodies are problematic since they combine the toxicity of chemotherapeutic agents with immune-related adverse events (IRAE) triggered by antibodies.

Only a few drugs targeting protein synthesis are currently in development or in clinical use. All of them however target components of the general translational machinery that are also essential to normal cells and therefore conducive to toxicity and resistance. For example, homoharringtonine (HHT; Synribo, omacetaxine mepesuccinate) binds to the 80S ribosome in eukaryotic cells and inhibits protein synthesis by interfering with chain elongation (19). Rapamycin and its analogs, whose mechanism is PI3K/mTOR inhibition, inhibit the initiation of step cap-dependent translation (20). However, under stress and hypoxia, cap-independent initiation predominates making cells refractory to mTOR/PI3K inhibitors. In contrast, hnRNP A18 inhibitors are not expected to be affected by these conditions since hnRNP A18, which is over expressed under hypoxic conditions (5), functions through a different mechanism involving recognition of an RNA signature motif within the 3'UTRs of its targeted transcripts.

The prior art is thus deficient in drugs that target both cancer progression and tumor immune response with minimal toxicity to normal cells. The present invention fulfills this long-standing need and desire in the art.

SUMMARY OF THE INVENTION

The present invention is directed to a protein translation inhibitor. The protein translation inhibitor comprises a compound with a chemical structure that binds to an RNA Recognition Motif (RRM) in a heterogeneous ribonucleoprotein A18.

The present invention also is directed to a pharmaceutical composition comprising the protein translation inhibitor as described herein and a pharmaceutically acceptable carrier.

The present invention is directed further to a method for treating a cancer in a subject in need thereof. The method comprises administering to the subject a pharmaceutically acceptable amount of a protein translation inhibitor, thereby inhibiting translation of a protein associated with the cancer.

BRIEF DESCRIPTION OF THE DRAWINGS

These and other features, aspects, and advantages of the embodiments of the present disclosure is better understood when the following detailed description is read with reference to the accompanying drawings in which like characters represent like parts throughout the drawing, wherein:

FIG. 1A shows surface representation of the crystal structure of the RRM of hnRNP A1 (hnRNP A1) bound to RNA. FIG. 1B shows surface representation of the crystal structure of the RRM of hnRNP A18 with residues predicted to bind RNA. FIG. 1C is a SILCS FragMaps overlaid on the RNA recognition motif domain of hnRNP A18. FIG. 1D shows a pharmacophore model derived using SILCS-Pharm based on FragMaps in virtual screening for small molecules that can potentially bind to hnRNP A18 RRM. FIG. 1E shows a predicted inhibitor aligned with the pharmacophore model on the crystal structure of hnRNP A1 alone. FIG. 1F shows a predicted inhibitor aligned with the modeled RNA binding mode on the crystal structure of hnRNP A1 RRM.

FIG. 2A represents resonance assignments together with a two dimensional [$^1$H-$^{15}$N] Heteronuclear single quantum coherence (HSQC) spectrum of hnRNP A18 RRM (black) overlaid with a [$^1$H-$^{15}$N] HSQC of hnRNP A18 with Compound 1. FIG. 2B is a representative fluorescence anisotropy measurement for reactions containing recombinant GST-full length hnRNP A18 and fluorescein tagged hnRNP A18 RNA motif 1 in presence of increasing concentrations of Compound 1. FIG. 2C is a representative RNA band shift performed with Iron Responsive Protein (IRP) and the Iron Responsive Element (IRE) in the presence of increasing concentrations of Compound 1. FIG. 2D shows chemical shift perturbations of backbone $^1$H-N protons in $^{15}$N-labeled hnRNP A18 upon the addition of Chembridge 785888 as measured in 2D Transverse relaxation optimized spectroscopy (TROSY) NMR experiments; FIG. 2E shows chemical shift perturbations in backbone $^{15}$N resonances as measured in 2D TROSY NMR experiments. FIG. 2F shows an overlay of ribbon diagrams of the RNA recognition motifs of hnRNP A1 and hnRNP A18 illustrating sidechains of residues that interact with RNA. FIG. 2G shows a space filling diagram of hnRNP A18 illustrating residues that show either $^1$H and/or $^{15}$N chemical shift perturbations greater than 0.15 PPM.

FIG. 3A shows RNA band shift performed with recombinant full length His-hnRNP A18 incubated with biotinylated hnRNP A18 RNA motif 1 and increasing concentrations of Compound 1. FIG. 3B shows RNA band shift performed with either recombinant full length His-hnRNP A18 incubated with biotinylated hnRNP A18 RNA motif 1 or IRP in the presence of biotinylated Iron Responsive Element exposed to increasing concentrations of Compound 6. FIG. 3C is a Coomassie blue staining of purified recombinant His-hnRNP A1. FIG. 3D is a Coomassie blue staining of purified recombinant hnRNP A18. FIG. 3E is a RNA band shift as in FIG. 3B with either hnRNP A18 recombinant protein or IRP and the indicated biotinylated RNA. FIG. 3F shows RNA band shift performed with either recombinant hnRNP A1 or hnRNP A18 and biotinylated hnRNP A18 RNA motif 1.

FIG. 4A shows a RNA band shift performed with either recombinant full length His-hnRNP A18 incubated with biotinylated hnRNP A18 RNA motif 1 or Iron Responsive Protein in the presence biotinylated Iron Responsive Element exposed to increasing concentration of Compound 5. FIG. 4B shows a representative fluorescence anisotropy experiments in the presence of increasing concentrations of Compound 5.

FIG. 5A shows a RNA band shift performed with either recombinant full length His-hnRNP A18 incubated with biotinylated hnRNP A18 RNA motif 1 or Iron Responsive Protein in the presence biotinylated Iron Responsive Element exposed to increasing concentration of Compound 2. FIG. 5B shows a representative fluorescence anisotropy experiments in the presence of increasing concentrations of Compound 2.

FIG. 6A shows a RNA band shift performed with either recombinant full length His-hnRNP A18 incubated with biotinylated hnRNP A18 RNA motif 1 or Iron Responsive Protein in the presence biotinylated Iron Responsive Element exposed to increasing concentration of Compound 3. FIG. 6B shows a representative fluorescence anisotropy experiments in the presence of increasing concentrations of Compound 3.

FIG. 7A shows a RNA band shift performed with either recombinant full length His-hnRNP A18 incubated with biotinylated hnRNP A18 RNA motif 1 or Iron Responsive Protein in the presence biotinylated Iron Responsive Element exposed to increasing concentration of Compound 4. FIG. 7B shows a representative fluorescence anisotropy experiments in the presence of increasing concentrations of Compound 4.

FIG. 8A shows a Cellular Engagement Thermal Shift Assay (CETSA) performed in LOX-IM-VI cells over expressing GFP-hnRNP A18 in presence of Compound 5, Compound 2 and Compound 4. FIG. 8B shows a CAT-Trx 3'UTR reporter assay in the presence of increasing concentrations of Compound 5, Compound 2, Compound 3, Compound 6 or Compound 4. FIG. 8C shows a western blot analysis of LOX-IM-VI cells treated with increasing concentrations of Compound 2. FIG. 8D shows a western blot analysis of LOX-IM-VI cells treated with increasing concentrations of Compound 5. FIG. 8E shows a western blot analysis of LOX-IM-VI cells treated with increasing concentrations of Compound 3. FIG. 8F shows a western blot analysis of LOX-IM-VI cells treated with increasing concentrations of Compound 4. FIG. 8G shows a western blot analysis of LOX-IM-VI cells stably transfected with scrambled shRNA (sc) or shRNA-hnRNP A18 (shA18).

FIGS. 9A-9H demonstrates regulation of CTLA-4 expression by hnRNP A18. FIG. 9A shows a sequence alignment of six possible versions of the putative motif SEQ ID NOS: 9-14 and the motif found in Trx (SEQ ID NO: 15) and CTLA-4 3'UTR (SEQ ID NO: 16). FIG. 9B is an RNA immunoprecipitation (IP) performed on prostate cancer PC-3 cells with IgG or A18 antibodies. FIG. 9C shows growth of prostate cancer PC-3 tumors in a mouse xenograft. FIG. 9D show representative western blot analysis of CTLA-4 and hnRNP A18 in excised PC-3 tumors. FIG. 9E shows representative western blot analysis of CTLA-4 and hnRNP A18 in prostate cancer PC-3 tumors treated with Compound 3. FIG. 9F shows representative western blot analysis of CTLA-4 and hnRNP A18 in prostate cancer PC-3 tumors treated with Compound 5. FIG. 9G shows representative western blot analysis of CTLA-4 and hnRNP A18 in melanoma LOX-IM-VI tumors treated with Compound 2. FIG. 9H shows representative western blot analysis of CTLA-4 and hnRNP A18 in pancreatic cancer MiaPaca tumors treated with Compound 4.

FIG. 10A shows cell viability analysis performed on colorectal carcinoma RKO treated with Compound 2, Compound 3, Compound 5, and Compound 4. FIG. 10B shows cell viability analysis performed on melanoma LOX-IM-VI treated with Compound 2, Compound 3, Compound 5, and Compound 4.

FIG. 10C shows cell viability analysis performed on Glioblastoma D54 treated with Compound 2, Compound 3, Compound 5, and Compound 4. FIG. 10D shows cell viability analysis performed on pancreatic cancer MiaPaca treated with Compound 2, Compound 3, Compound 5, and Compound 4. FIG. 10E shows cell viability analysis performed on triple negative breast cancer MDA-MD-231 cells treated with Compound 2, Compound 3, Compound 5, and Compound 4. FIG. 10F shows cell viability analysis performed on normal human mammary epithelial HMEC treated with Compound 2, Compound 3, Compound 5, and Compound 4.

DETAILED DESCRIPTION OF THE INVENTION

Figure 1A:
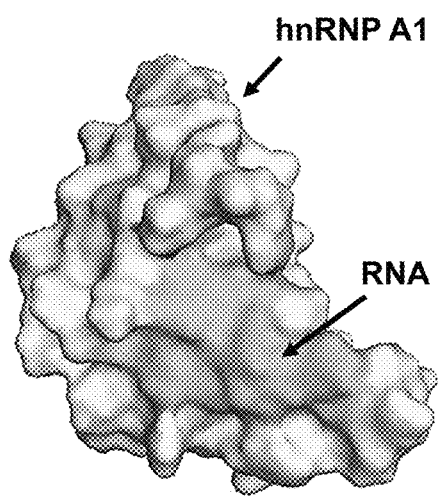
FIGS. 1A-1F illustrate site-Identification by ligand competitive saturation (SILCS) to identify potential small molecule inhibitors that disrupt heterogeneous ribonucleoprotein A18 (hnRNP A18)-RNA interactions.
Figure 1B:
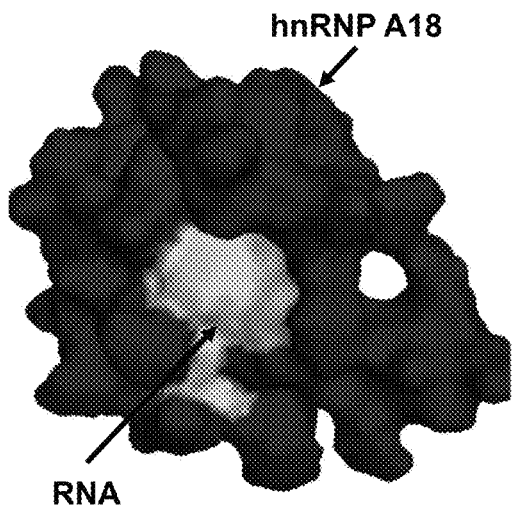

As used herein, the term "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method described herein can be implemented with respect to any other method described herein.

As used herein, the term "or" in the claims is used to mean "and/or" unless explicitly indicated to refer to alternatives only or the alternatives are mutually exclusive, although the disclosure supports a definition that refers to only alternatives and "and/or."

As used herein, "comprise" and its variations, such as "comprises" and "comprising," is understood to imply the inclusion of a stated item, element or step or group of items, elements or steps but not the exclusion of any other item, element or step or group of items, elements or steps unless the context requires otherwise. Similarly, "another" or "other" may mean at least a second or more of the same or different claim element or components thereof.

As used herein, the terms "protein translation inhibitor", "inhibitor" and "compound" refer to a chemical entity effective to inhibit translation of an mRNA transcript to a protein associated with a cancer and/or a cancer cell, for example, but not limited to, a protein associated with cancer cell proliferation and/or a tumor immune checkpoint protein as described herein. For example, the inhibitor and the compound may be, but are not limited to, a small molecule drug or a small molecule inhibitor.

As used herein, the term "contacting" refers to any suitable method of bringing an inhibitor, a compound or a pharmaceutical composition into contact with a cell, for example, but not limited to, a cancer cell. For in vivo applications, any known method of administration is suitable as described herein.

As used herein, the term "pharmaceutically acceptable" refers to molecular entities and compositions that do not produce an adverse, allergic or other untoward reaction when administered to an animal, such as, for example, a human, as appropriate. The preparation of a pharmaceutical composition that contains an inhibitor is known to those of skill in the art in light of the present disclosure, as exemplified by Remington's Pharmaceutical Sciences, 18th Ed. Mack Printing Company, 1990, incorporated herein by reference.

As used herein, the term "subject" refers to any human or non-human recipient of the inhibitors, compounds or pharmaceutical compositions thereof described herein.

As used herein, the term "therapeutically effective amount" refers to that amount of the inhibitor and/or compound being administered to the subject sufficient to prevent progression of a cancer, to inhibit or decrease cancer cell proliferation and/or metastasis, to effect a decrease in tumor growth or to improve an immune reaction against the cancer, tumor or cancer cell.

In one embodiment of this invention, there is provided a protein translation inhibitor, comprising a compound with a chemical structure that binds to an RNA Recognition Motif in a heterogeneous ribonucleoprotein A18.

In this embodiment, the protein translation inhibitor may be a small molecule compound shown in Table 1.

TABLE 1

Protein Translation Inhibitors

| Compound | Structure |
| --- | --- |
| Compound 1 (Chembridge 7858888) | 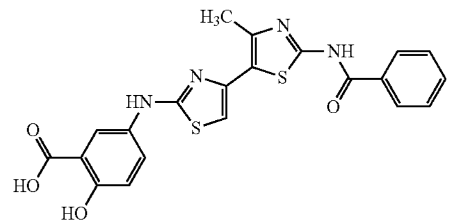 [SMILES: Cc1nc(NC(=O)c2ccccc2)sc1-c1csc(Nc2ccc(O)c(C(=O)O)c2)n1] |
| Compound 2 (Chembridge 7646184) | 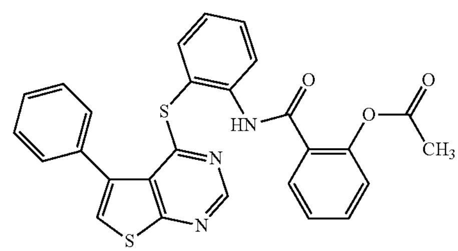 [SMILES: CC(=O)Oc1ccccc1C(=O)Nc1ccccc1Sc1ncnc2scc(-c3ccccc3)c12] |
| Compound 3 (Chembridge 6823240) | 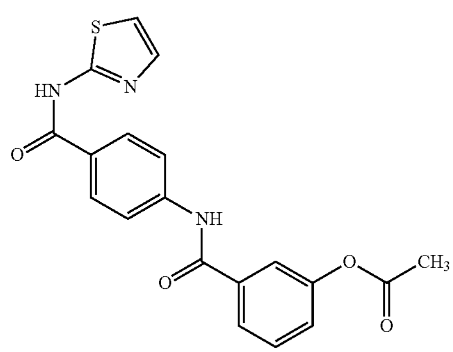 [SMILES: CC(=O)Oc1cccc(C(=O)Nc2ccc(C(=O)Nc3nccs3)cc2)c1] |
| Compound 4 (OTAVA 219853) | 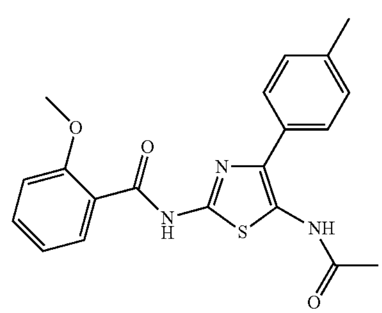 [SMILES: COc1ccccc1C(=O)Nc1nc(-c2ccc(C)cc2)c(NC(C)=O)s1] |

TABLE 1-continued

Protein Translation Inhibitors

| Compound | Structure |
|---|---|
| Compound 5 (VITAS STK508411) | 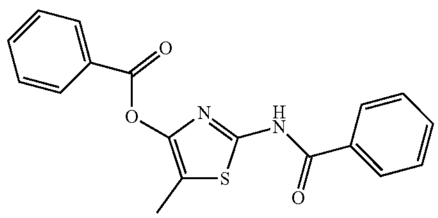 [SMILES: Cc1sc(NC(=O)c2ccccc2)nc1OC(=O)c1ccccc1] |
| Compound 6 (OTAVA 2192700) | 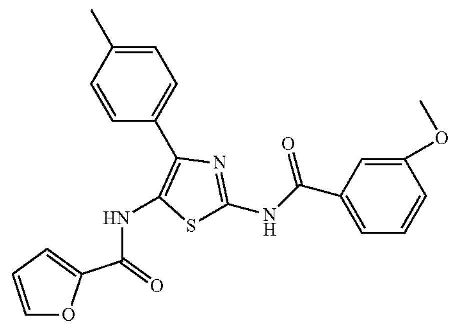 [SMILES: COc1cccc(C(=O)Nc2nc(-c3ccc(C)cc3)c(NC(=O)c3ccco3)s2)c1] |

In an aspect of this embodiment, the compound inhibits binding of the heterogeneous ribonucleoprotein A18 to an mRNA transcript for a protein associated with cancer cell proliferation. Representative examples of the protein associated with cancer cell proliferation include but are not limited to thioredoxin, vascular endothelial growth factor, or replication protein A or a combination thereof.

In another aspect of this embodiment, the compound inhibits binding of the heterogeneous ribonucleoprotein A18 to an mRNA transcript for a tumor immune checkpoint protein. Representative examples of the tumor immune checkpoint protein include but are not limited to cytotoxic T-lymphocyte-associated protein 4, programmed cell death protein 1, or programmed death-ligand 1, or a combination thereof.

In another embodiment of this invention, there is provided a pharmaceutical composition comprising the protein translation inhibitor as described supra and a pharmaceutically acceptable carrier.

In yet another embodiment of this invention, there is provided a method for treating a cancer in a subject in need thereof comprising the step of administering to the subject a therapeutically effective amount of a protein translation inhibitor, thereby inhibiting translation of a protein associated with the cancer.

In this embodiment, the protein translation inhibitor is described supra. Also in this embodiment, Representative examples cancers include but are not limited to melanoma, lung cancer, prostate cancer, intestinal cancer, colon cancer, pancreatic cancer, gall bladder cancer, bile duct cancer, brain cancer, glioblastoma, breast cancer, hepatocellular carcinoma, kidney cancer, bladder cancer, or lymphoma.

Provided herein are protein translation inhibitors that inhibit cancer progression by inhibiting translation of mRNA transcripts for proteins associated with cancer, for example, as depicted in Table 1. The inhibitors inhibit translation of the cancer-associated proteins by binding to a ribonucleoprotein (RNP) RNA binding domain (RBD) thereby blocking interactions with these mRNA transcripts.

In a non-limiting example, the inhibitors bind to a heterogeneous ribonucleoprotein A18 (hnRNP A18). The inhibitors are effective against the translation of cancer-associated proteins such as, but not limited to, cancer cell proliferation proteins, for example, thioredoxin (Trx), vascular endothelial growth factor (VEGF) and heterotrimeric replication protein A (RPA) and tumor immune checkpoint proteins, for example, cytotoxic T-lymphocyte-associated protein 4 (CTLA-4), programmed cell death protein 1 (PD-1) and programmed death-ligand 1 (PD-L1). A combination of mRNA transcripts for proteins involved in tumor cell proliferation and tumor immune checkpoint may also be targeted by the protein translation inhibitors. The inhibitor inhibits both cancer cell proliferation and tumor immune checkpoint proteins which is beneficial since a single compound inhibits the translation of mRNA for two distinct protein types, thereby reducing toxicity to normal tissue.

Also provided are pharmaceutical or therapeutic compositions of the protein translation inhibitors. As is known and standard in the art, the inhibitors are formulated with, although not limited to, a pharmacologically acceptable carrier, diluent or excipient or other vehicle. Any conventional carrier known in the art may be used for this purpose except insofar as the carrier is incompatible with the inhibitor. The pharmaceutical compositions may take a variety of forms such as, but not limited to, a solution, a suspension, a powder in pill form, or a gel.

Furthermore, the inhibitors or pharmaceutical compositions thereof provided herein have a therapeutic effective against a cancer and/or an anti-proliferative effect against a tumor or a cancer cell. Contacting the tumor or cancer cells with the inhibitor in vivo or in vitro results in the therapeutic and/or anti-proliferative effect. Thus provided herein is a method for treating a cancer in a subject patient by administering a therapeutically effective amount of the protein translation inhibitor at a dosage that inhibits protein translation of the proteins associated with the cancer, but not in normal tissues.

The cancer being treated may be a solid primary cancer or a metastatic cancer. Non-limiting examples of a cancer are melanoma, lung cancer, prostate cancer, intestinal cancer, colon cancer, pancreatic cancer, gall bladder cancer, bile duct cancer, brain cancer, glioblastoma, breast cancer, hepatocellular carcinoma, kidney cancer, bladder cancer, or lymphoma.

Generally, it is known in the art that a dosage amount or therapeutically effective amount of an inhibitor compound or a pharmaceutical composition of the present invention administered to a subject can be determined by physical and physiological factors such as body weight, severity of condition, the type of cancer being treated, previous or concurrent therapeutic interventions, idiopathy of the patient and on the route and timing of administration. The practitioner responsible for administration will, in any event, determine the concentration of the inhibitor in a composition and appropriate dose(s) for the individual subject.

The following example(s) are given for the purpose of illustrating various embodiments of the invention and are not meant to limit the present invention in any fashion.

EXAMPLE 1

Computer-Aided Drug Design

Site Identification by Ligand Competitive Saturation (SILCS) and related techniques (13) (14, 23-25) were used. SILCS has advantages such as including protein flexibility and protein and ligand solvation effects as compared with traditional docking methods. The crystal structure of the hnRNP A18 RRM domain (PDB ID: 1X55) (12) was used to initialize the SILCS simulation. The Reduce software (26) was used to choose optimal Asn, Gln, and His side-chain ring orientations and determine the optimal protonation states of His residues. The protein was immersed in a box of water containing eight organic solutes at approximately 0.25 M each. These included benzenes, propane, methanol, formamide, imidazole, acetaldehyde, methylammonium and acetate. The size of the simulation box was chosen so as to have the protein extrema separated from the edge by 8 A on all sides. Ten such protein-aqueous solution systems were generated with each system differing in the initial positions and orientations of the solutes and water in order to maximize conformational sampling of the aqueous solution and the protein.

The SILCS simulations were performed using MolCal program (SilcsBio LLC) and the GROMACS (27) simulation program with the CHARMM36 force field (28) (29), CHARMM general force field (CGenFF) (30) (31) and CHARMM TIP3P water model (32) to describe the protein, organic solutes and water. 3D functional group probability distributions of selected atoms from the organic solutes were extracted from the simulations to construct the FragMaps. The voxel occupancies of the eleven atom types were merged according to their chemical interaction types to create the following FragMap types: (1) generic nonpolar, APOLAR (benzene and propane carbons); (2) generic neutral donor, HBDON (methanol oxygen, formamide and imidazole amide nitrogens); (3) generic neutral acceptor, HBACC (methanol, formamide, acetaldehyde oxygens and imidazole neutral nitrogen); (4) positive donor, MAMN (methylammonium nitrogen); (5) negative acceptor, ACEO (acetate oxygens); (6) aromatic, BENC (benzene carbons); (7) aliphatic, PRPC (propane carbons); (8) MEOO (methanol oxygen); (9) FORN (formamide nitrogen); (10) FORO (formamide oxygen); (11) AALO (acetaldehyde oxygen); (12) IMIN (imidazole neutral acceptor nitrogen); and (13) IMIH (imidazole neutral donor protonated nitrogen). The voxel occupancies in the FragMaps were normalized and Boltzmann transformed to yield grid free energies (GFE) as required to quantitatively estimate relative ligand binding affinities term Ligand Grid Free Energies (LGFE). An exclusion map representing the fragment/water forbidden region from the SILCS simulations was generated to serve as an alternative to describe the protein surface versus the traditional representations of the protein surface. The exclusion map takes into account protein flexibility in combination with regions that water and the organic solutes can access, thereby describing potential regions to which a ligand can occupy a specific surface on the target protein that are inaccessible based on the crystal structure alone.

To search for potential hnRNP A18 small molecule inhibitors targeting the RNA binding pocket, the SILCS-Pharm protocol (25) was used to develop pharmacophore models for virtual screening. In addition, the SILCS exclusion map was also used in the model to represent the forbidden region that ligands cannot occupy. Pharmacophore based virtual screening was performed using Pharmer (33) against the University of Maryland CADD Center in silico database that contains 721,368 compounds (1,695,786 molecules considering different protonation states and tautomers) from the vendor Chembridge and 56,237 compounds (126,575 molecules) from the vendor Maybridge. The 154 compounds for experimental assays were selected based on the root-mean-square difference of the ligand pharmacophore points with the SILCS-Pharm features, chemical diversity based on BIT-MACCS chemical fingerprint cluster using MOE (Chemical Computing Group), predicted bioavailability considerations and commercial availability. A similarity screen target the query compound Compound 1 (Chembridge 7858888) was performed against the full UMB CADD Center 5.04 million compound database using BIT-MACCS chemical fingerprints with the program MOE. The similarity cutoff value was set at 80% and 264 compounds were identified based on those criteria.

PAMPA

The PAMPA assay was performed by Pion (Billerica, Mass.) on 81 compounds selected out of the 264 compounds showing at least 80% similarity to Compound 1, logP<5.0, and 4DBA closer to 0 (>−4.9). The compounds were dissolved at 10 mM in Dimethyl sulfoxide (DMSO, spectrophotometric grade) and filtered (0.2 μm pore size, hyrodophylic PVDF). The assays were carried in the PAMPA STIRWELL plates (lot A0440) and measured at pH 5.0 and 6.8 at room temperature for ~4 hours on a PAMPA EVOLUTION instrument. After permeation, a UV spectrum was scanned from 245 nm to 498 nm to determine the relative concentration in both the donor (GIT-0 lipid (PN 110669, lot# 520552) and acceptor sink buffer (PN 110139, lot# 520549). The effective permeability (Pe×10−6 cm/s) coefficients were then calculated from these results (34).

NMR: $^{15}$N-labeled A18 RNA Recognition Motif Purification $^{15}$N-labeled A18 RNA recognition motif (residues 1-92 of hnRNP A18 wildtype) was expressed and purified (>99%) with methods similar to those described previously (12). Briefly, the A18 RRM construct was cloned into the *Escherichia coli* (*E. coli*) expression plasmid pHGK-IF (unpublished) in-frame with a 6x-His-tagged protein G, B1 domain (GB1) fusion protein and Tobacco etch virus (TEV) protease-cleavage site upstream. The pHGK-A18 RRM construct was transformed into *E. coli* BLD21(DE3) cells and a single colony was grown in 5 L of M9 minimal medium (Sambrook & Russel citation) with $^{15}$N-labeled (>99%) ammonium chloride as the single nitrogen source at 37° C. When the $A_{600}$ reached 0.8, the incubation temperature was reduced to 18° C. His$_6$GB1-A18 RRM expression was induced by the addition of 1 mM IPTG (isopropyl β-D-1-thiogalactopyranoside) and cells were grown for an additional 16 hours. Cells were pelleted by centrifugation at 10,000 g for 20 minutes. The cells were resuspended in a denaturing buffer (20 mM Tris pH 7.4, 500 mM NaCl, 5 mM Imidazole, 6 M Urea, and 0.5 mM AEBSF) and lysed via sonication. The cells were centrifuged for 18,000 g for 45 minutes to pellet cellular debris and the supernatant was filtered with a 0.45 μm syringe. The filtered supernatant was applied to a 5 mL HisTrap FF column (GE Healthcare, catalog No. 17-52255-01), which was equilibrated with the denaturing buffer. A refolding buffer (20 mM Tris pH 7.4, 500 mM NaCl, 5 mM Imidazole) was applied to the column as a linear gradient over 20 column volumes (100 mL). His$_6$GB1-A18 RRM was eluted from the column through a linear gradient of elution buffer (20 mM Tris pH 7.4, 500 mM NaCl, 500 mM Imidazole) over 10 column volumes (50 mL).

The eluted fractions were analyzed by SDS-PAGE and fractions with His$_6$GB1-A18 RRM were combined, dialyzed into the refolding buffer (see above) overnight, and treated with His-tagged TEV protease simultaneously to remove A18 RRM from the His$_6$GB1 fusion protein. The sample was applied to a HisTrap HP column (GE Healthcare, catalog No. 17-5247-01) in refolding buffer and the flow through contained purified A18 RRM. The protein was dialyzed into ultrapure water, concentrated using Amicon Ultra centrifugal filter units with a 3 kDa molecular weight cut off, and quantified by the Bio-Rad Protein Assay (Bio-Rad Inc., Hercules, Calif.). The A18 RRM was stored at a concentration of ~0.33 mM in ultrapure water at −80° C. until use.

NMR Spectroscopy

The hnRNP A18 RRM samples used for compound screening via high field NMR spectroscopy using a series of single-quantum coherence (HSQC) experiments contained 0.1 to 0.2 mM $^{15}$N-labeled hnRNP A18 RRM, ultrapure water, 10% $D_2O$, 5% $d_6$-DMSO and up to 5 mM of each of the forty compounds tested, as based on their solubility. All of the HSQC data were collected at 25° C. with a Bruker Avance 800 US2 NMR spectrometer (800.27 MHz, $^1$H) equipped with pulsed-field gradients, four frequency channels, an automatic sample changer, and a TXI cryogenic probe. Backbone resonance assignments in the presence of compounds were achieved via compound titrations and monitoring chemical shift changes until solubility limits were reached (<5 mM compound). Data were processed with NMRPipe (35), and proton chemical shifts and their perturbations upon binding the various compounds were reported with respect to the $H_2O$ or HDO signal taken as 4.698 ppm relative to external TSP (0.0 ppm).

Measurement of RNA Binding Activity In Vitro

RNA Substrates: RNA oligonucleotides were synthesized and purified by Integrated DNA Technologies, Dharmacon (Skokie, Ill.). Lyophilized pellets were resuspended in 10 mM Tris (pH 8.0). RNA concentrations and fluorophore labeling efficiencies were quantified by absorbance, incorporating fractional contributions from fluorescein (Fl) labels to A260 as described (36). RNA probe sequences are listed in Table 2.

TABLE 2

RNA probe sequences

| Name | Sequence (5' to 3') |
|---|---|
| SEQ ID NO: 1<br>hnRNP A18 motif 1<br>Fluorescein* | GCAGAUCCAGGGUGGGAUUUUCUUGAGGA<br>AGUUACAAAUAAGCUUGUUACA-T-<br>Fluorescein |
| SEQ ID NO: 2<br>hnRNP A18 motif 1<br>Biotin | GCAGAUCCAGGGUGGGAUUUUCUUGAGGA<br>AGUUACAAAUAAGCUUGUUACA-<br>Biotin |
| SEQ ID NO: 3<br>IRE 51nt<br>Biotin | UCCUGCUUCAACAGUGCUUGGACGGAACU<br>CCUGCUUCAACAGUGCUUGGAC-<br>Biotin |
| SEQ ID NO: 4<br>IRE 28nt<br>Biotin | UCCUGCUUCAACAGUGCUUGGACGGAAC-<br>Biotin |

*T-Fluorescein: Fluorescein linked at position 5 of the Thymine ring by a 6-carbon spacer arm RNA Band Shift (EMSA)

RNA band shifts were performed according to the manufacturer recommendations (LightShift Chemiluminescent RNA EMSA kit, Thermo Scientific, Rockford, Ill.). Briefly recombinant His-hnRNP A18 or His-hnRNP A1 (1 μg) were incubated with biotinylated RNA (hnRNP A18 motif 1, IRE 28 or 51 nucleotides) in 20 μl and run on native polyacrylamide gels transfer to nylon probes and hybridize with streptavidin HRP antibody.

RNA-IP

The RNA-IP was performed on PC-3 cell extracts with the Magna RIP RNA-Binding Protein Immunoprecipitation Kit (Millipore Sigma, Burlington, Mass.) as recommended by the manufacturer.

CTLA-4 primers:

(SEQ ID NO: 5)
5'-TGACAGCCAGGTGACTGAAG-3'

(SEQ ID NO: 6)
5'-GCCTCAGCTCTTGGAAATTG-3'

The size of the amplified product was 493 for CTLA-4.
GAPDH primers:

(SEQ ID NO: 7)
5'-ACATCAAGAAGGTGGTGAAGCAGG-3'

(SEQ ID NO: 8)
5'-CCAGCAAGGATACTGAGAGCAAGAG-3'

The size of the amplified product was 324 for GAPDH.

Fluorescence Anisotropy

Quantitative assessments of hnRNP A18-RNA binding equilibria were performed using fluorescence anisotropy essentially as described (36). Briefly, binding reactions (100 μl) were assembled as described for RNA band shift (EMSAs) but in absence of glycerol and using fluorescein labeled rather than biotin labeled RNA substrates. Reactions were incubated at 25° C. for 30 min; preliminary kinetics runs verified that equilibrium was attained within this period. Subsequently, total reaction anisotropy (At) and fluorescence intensity were measured using a Beacon 2000 Fluorescence Polarization System (Panvera) equipped with a 490-nm excitation filter and a 535-nm emission filter. Drug-dependent changes in $A_t$ were analyzed by nonlinear regression using the four parameter logistic equation (Eq.1) and PRISM software (GraphPad).

$$A_t = A_R + \frac{A_{PR} - A_R}{1 + 10^{\log(IC_{50}/[drug]) \cdot h}} \quad \text{(Equation 1)}$$

Here, $A_{PR}$ represents the intrinsic anisotropy of the protein:RNA complex in the absence of tested compounds, $A_R$ is the anisotropy of the RNA ligand in the absence of protein, [drug] is the concentration of each tested compound, and h is the Hill slope.

CAT ELISA

CAT-ELISA was performed as recommended by the manufacturer (Sigma-Aldrich). Briefly, human melanoma LOX-IM VI cells stably transfected with hnRNP A18-GFP (9) were transiently transfected with a CAT reporter vector harboring Trx 3'UTR (16). Twenty-four hours later the cells were distributed in 6 well plates and treated with increasing amounts of drugs. The next day, the cells were washed, and protein extracted. The CAT-ELISA was performed on 25 μg of proteins in triplicate in microplates precoated with a polyclonal antibody for CAT and revealed with anti-CAT-DIG, anti-DIG-POD and the peroxidase substrate ABTS as recommended. Cleavage of the substrate catalyzed by the peroxidase enzyme was measured on a plate reader at 405 nm.

Cell Viability and Tumor Growth In Vivo

Cells viability was measured on normal human mammary epithelial cells (HMEC: ATCC, Gaithersburg, Md.) grown as recommended by the manufacturer and human cancer cells including melanoma LOX-IM-VI, colon cancer RKO, Gliobalstoma D54, pancreatic cancer MiaPaca and triple negative breast cancer MDA-MD-231 cells (5) with the Apo-Tox-Glo kit (Promega, Madison, Wis.) as recommended by the manufacturer. The cells were plated (10,000 cells per well) on a 96 well plate and exposed to increasing concentration of chemical probes for 24 hrs and reacted with the viability reagent as recommended. Fluorescence was measured on a plate reader at 400 nm Ex/505 nm Em.

Tumor growth in vivo was performed as described previously (5) with the assistance of the University of Maryland Marlene and Stewart Greenebaum Comprehensive Cancer Center Translational Laboratory Shared Services, reviewed and approved by an Institutional Animal Care and Use Committee (Protocol # 1016012) at the University of Maryland Medical School. Briefly, PC3 cells ($3 \times 10^6$) stably transfected with a mixture of four plasmids expressing different hnRNP A18 shRNA were injected s.c. in the flanks of four-week-old female athymic mice (nu/nu). Tumors were allowed to grow for 40 days and volumes measured by caliper at different intervals. The mice were then sacrificed, and the tumors excised for protein analysis by Western blots analysis.

Cellular Thermal Shift Assay (CETSA)

Cellular thermal shift assay (CETSA) was performed with LOX-IM-VI hnRNP

A18 cells cultured in RPMI medium supplemented with 10% FBS. For an initial determination of the melting profile of hnRNP A18, cells dispensed into 96-well PCR plate in the above medium (5000 cells/well/50 µl), were subjected to temperature gradient (40-60° C.) for 10 min. Cold non-denaturing lysis buffer (PBS supplemented with 0.1% TritonX-100 and 1× protease inhibitors) was added to wells, and the plate was rocked and incubated for 15 min on ice. Subsequently, centrifugation was performed at 14.000 rpm to sediment the unstable protein content. Supernatant was collected, and SDS-PAGE gel was run, and immuno-detection was performed using poly-clonal anti-hnRNP A18 antibody (Sigma, CIRP). hnRNP A18 band was quantified on LI-COR C-Digit Blot Scanner, and subsequently $T_{agg}(50)$ and $T_{agg}(75)$ values were calculated for hnRNP A18.

In a subsequent run, cells were treated at various doses (80, 40, 20, 10, 5, 2.5 and 1.25 µM) of Compound 2 (Chembridge 7646184), Compound 4 (OTAVA 219853) and Compound 5 (VITAS STK508411) together with DMSO control, for 3 hours. Cells were then subjected to heat shock at $T_{agg}(75)$ for 10 min, and unstable protein was removed by centrifugation step. Following an immuno-blotting step, bands of stable hnRNP A18 protein was quantified, normalized to loading control and plotted using GraphPad Prism software. $EC_{50}$ values of Compound 2, Compound 4 and Compound 5 compounds were calculated.

EXAMPLE 2

Rational Approaches to Identifying Protein Translation Inhibitors

A rational approach was developed for identifying protein translation inhibitors of hnRNP A18-RNA interactions. Using Computer-Aided Drug Design (CARD) based on SILCS, structural biology and cell-based assays compounds were identified that specifically target hnRNP A18 FARM, disrupt its RNA binding activity, down regulate expression of targeted proteins such as Trx and cytotoxic T-lymphocyte-associated protein 4 (CTLA-4) and selectively inhibit cancer cells proliferation. These protein translation inhibitors greatly facilitate the elucidation of a new mechanism to simultaneously inhibit cancer cells proliferation and an immune checkpoint.

To address this need, hnRNP A18, a RNA-Binding Protein (RBP) recently described as a new regulator of protein translation in cancer cells (3) was targeted. Immunohistochemical studies have shown that RBPs are abnormally expressed in several cancer relative to adjacent normal tissues, and their expression correlates with patient prognosis (4). Accordingly, this data indicates that hnRNP A18 is upregulated in most cancer tissues as compared to normal tissues and its down regulation significantly reduces tumor growth in mouse xenograft models (5). hnRNP A18 was originally cloned by hybridization subtraction based on rapid induction in UV radiated CHO cells (6). The human hnRNP A18 was subsequently cloned and characterized (7). The protein has also been identified in mouse following exposure to mild cold shock and is also known as CIRP for Cold Inducible RNA Binding Protein (8).

Under normal physiological conditions, hnRNP A18 is predominantly a nuclear protein but translocate to the cytosol in response to cellular stress such as UV radiation and hypoxia (9-11). In the cytosol, it recognizes a 51-nucleotide signature motif in the 3'UTR of targeted transcripts important for cancer progression. In addition to stabilizing these transcripts, hnRNP A18 increases their translation by interacting with the eukaryotic Initiation Factor 4G (eIF4G), a member of the general translational machinery, to initiate translation at the 5 UTR (3). hnRNP A18 thus represents a potential therapeutic target for the treatment of cancer.

Although perturbations of RBP-RNA activity have been associated with cancer progression, development of small molecules that could disrupt these interactions has been rather challenging mainly due to the notorious disordered domains of RBPs and the flexibility of the RNA molecules (17). Nonetheless, these complexities endow RBPs the versatility required to control the metabolism of a large array of transcripts transcending more than one cancer hallmark (18). Because RBPs disordered domains are primarily associated with the RGG boxes, attention was focused on hnRNP A18 RRM to identify compounds that could disrupt hnRNP A18-RNA interactions. Using Computer-Aided Drug Design (CADD) based on SILCS, structural biology and cell-based assays four protein translation inhibitors were identified, which specifically target hnRNP A18 RRM, disrupt its RNA binding activity, down regulate expression of targeted proteins and selectively inhibit cancer cells proliferation (FIGS. 8A-8G, 10A-10F). The data indicate the hnRNP A18 regulates transcripts associated with cancer progression and an immune checkpoint through post-transcriptional regulation (FIGS. 8A-8G, 9A-9H).

Combining protein translation inhibitors with immune checkpoint inhibitors is an attractive strategy that is currently being studied in pre-clinical and clinical settings (21) (NCT02423954, and NCT02890069, clinicaltrials.gov), but there is currently no single molecule that can accomplish these two biological functions. As stated above, the current approaches target the general protein translation machinery and are limited by drug dosing, optimal scheduling and added toxicity. For instance, humanized anti-CTLA-4 antibodies have shown impressive results in various tumors including melanoma and small cell lung cancer but can also induce significant immune-related adverse events (RAE) such as colitis, dermatitis or endocrinopathies (22). Although CTLA-4 is primarily located in intracellular compartments, only a small proportion is rapidly recycled to the cell surface to mediate major inhibitory effects on T-cell activation (22). Inhibiting CTLA-4 translation thus provides an alternative mechanism to increase cytotoxic T-cells activity against tumor antigen while preventing or reducing RAE. The protein translation inhibitors identified here show specificity and efficacy against hnRNP A18 RNA binding activity in vitro and in cells. Based on hnRNP A18 low abundance in normal cells (5) it was expected that these protein translation inhibitors show preferential killing of cancer cells over normal cells, Indeed, data obtained support this expectation (FIGS. 10A-10F) and indicate that these protein translation inhibitors could serve as templates to better understand the underexplored biological function of RNA-RBPs in cancer cells proliferation, elucidate a new mechanism to simultaneously inhibit cancer cells proliferation and an immune checkpoint and develop a new generation of anticancer agents with suitable therapeutic index.

EXAMPLE 3

Site Identification by Ligand Competitive Saturation (SILCS)

The highly conserved hnRNP family of proteins share a high degree of similarity within their RNA Binding Domain (RBD). A distinctive characteristic of hnRNP A18 is that it contains a single RBD and a single Arginine Glycine rich (RGG) domain rather than the two canonical RBDs found in most hnRNP proteins (3). Structural studies showed that the RGG domain is intrinsically disordered, which prevents crystallization. Nonetheless, the structural similarities between hnRNP A1 and hnRNP A18 RNA recognition motif (12) (FIGS. 1A-1F, 2A-2B) and were used to guide design of hnRNP A18 inhibitors. Alignments of hnRNP A18 with hnRNP A1 bound to RNA, indicated that residues F10, F50, F52 and R48 on hnRNP A18 are expected to be important residues for RNA binding (12). Inhibitors targeting binding site around these residues are thus expected to block hnRNP A18-RNA interactions.

Figure 1C:
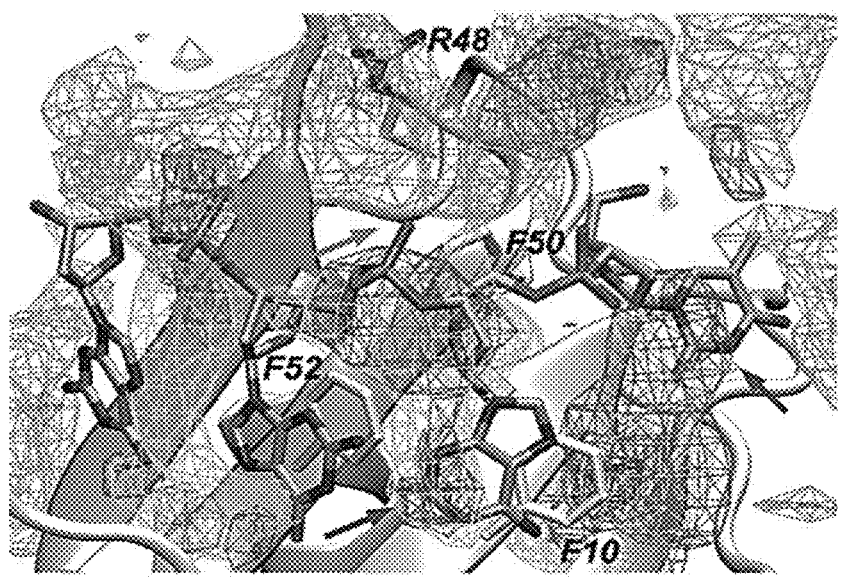

A state-of-the-art Computer Aided Drug Design (CADD) algorithm, Site Identification by Competitive Ligand Saturation (13) (FIGS. 1C-1F) was used to calculate a 3D map of the functional group affinity patterns. FragMaps, using the 3D structure of hnRNP A18 RNA recognition motif determined by X-ray crystallography were obtained (11). FIG. 1C shows a SILCS 3D probability map of fragment binding (FragMaps) overlaid on the RNA recognition motif domain of hnRNP A18. Aliphatic, aromatic, hydrogen bond donor, acceptor, positively charged and negatively charged FragMaps are contoured at −1.2 kcal/mol GFE values. Different types of FragMaps are shown in the targeted binding region on the protein surface, including negative maps related to the presence of R48 and aromatic and aliphatic FragMaps near residues F10, F50 and F52 indicating that compounds with nonpolar functional groups are likely good binders and form hydrophobic interactions with protein residues in this region. These FragMaps guide the identification of a potential hnRNP A18-RNA binding mode as seen in FIG. 1C.

Figure 1D:
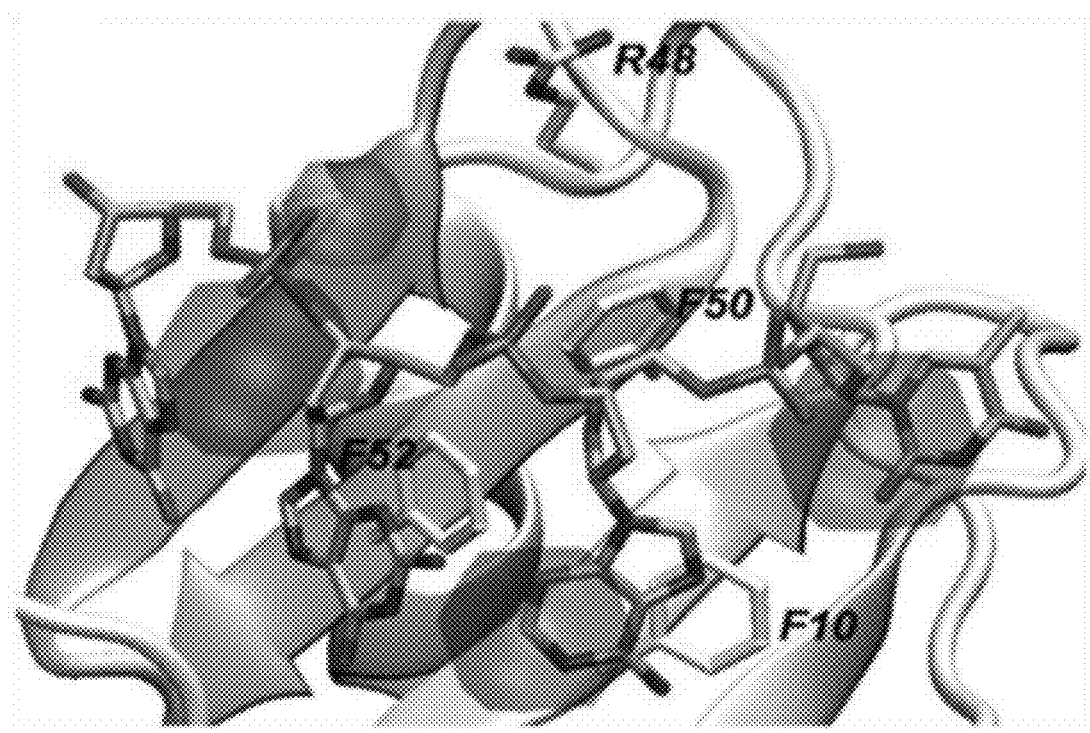
Figure 1E:
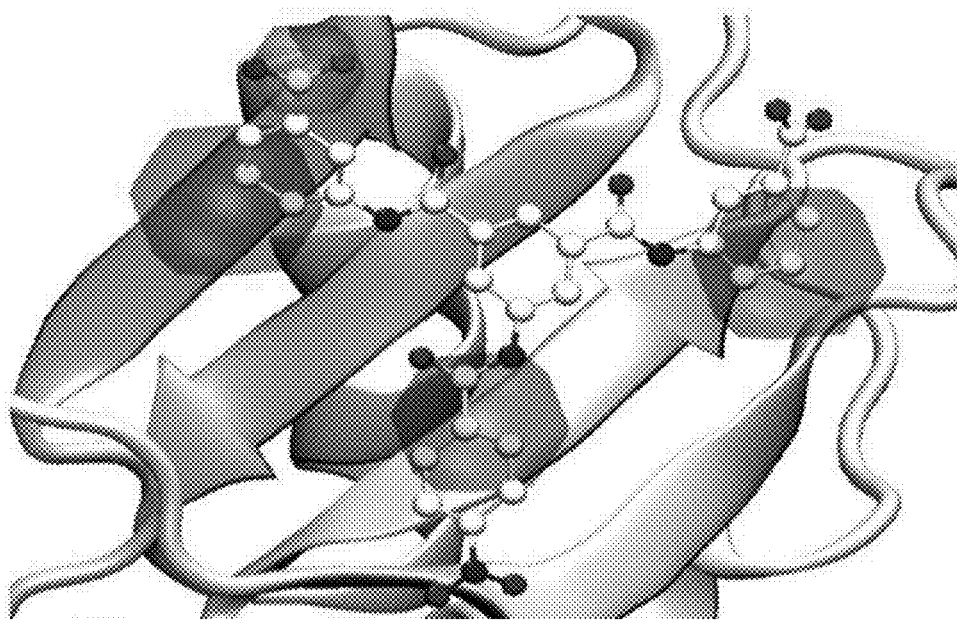
Figure 1F:
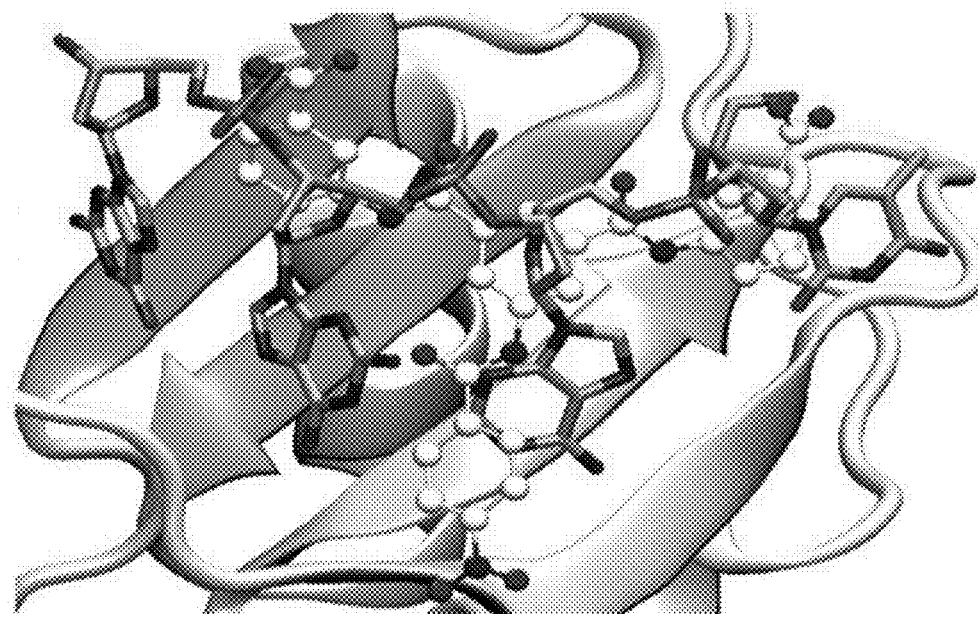
Figure 2A:
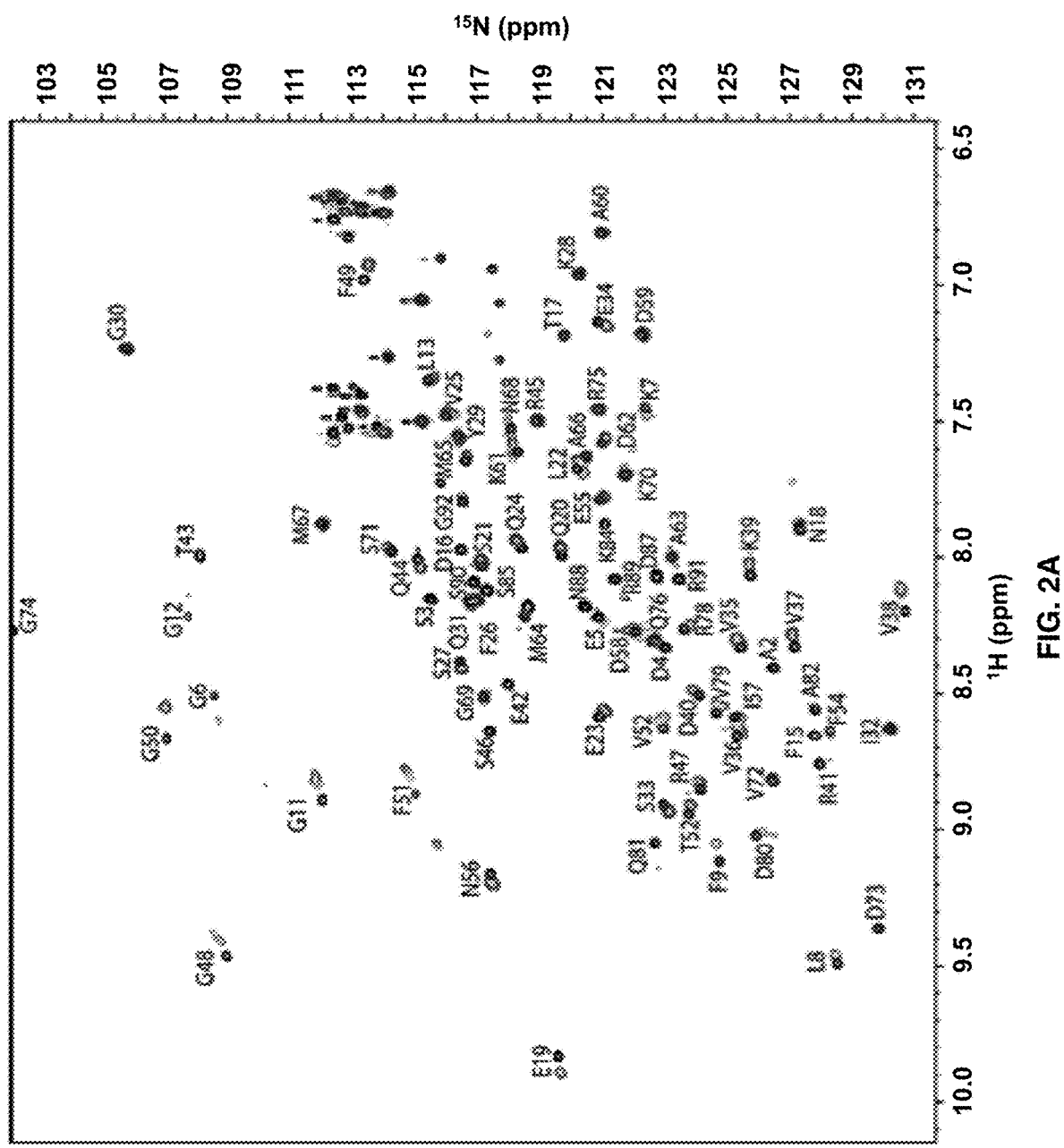
FIGS. 2A-2G shows interactions between Compound 1 and hnRNP A18.
Figure 2B:
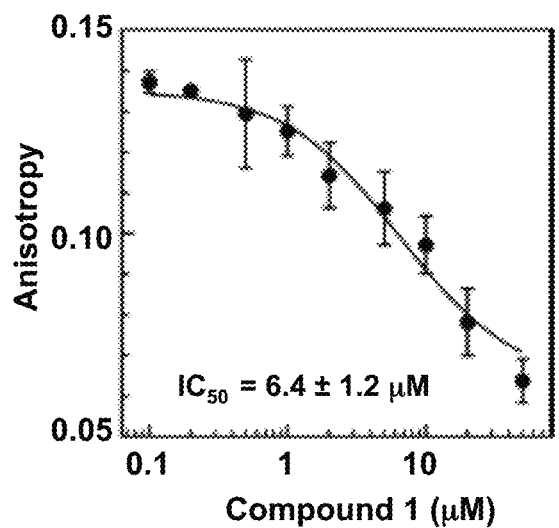

Based on the FragMaps, a 4-point pharmacophore model was developed to perform a virtual screening of small molecules that can potentially bind to hnRNP A18. Using a 4-point model (14) a model with three aromatic features and one anionic feature was identified for hnRNP A18. These four pharmacophore features capture the main crystal binding mode of RNA which is predicted to be important for inhibitor binding (FIG. 1D). In the virtual screen against the UMB CADD Center database of commercially available compounds (780,000 molecules), 154 molecules were selected in the pharmacophore screen based on the number and types of pharmacophore features. These compounds were then ranked using the Pharmer RMSD score which measures the spatial similarity between the screened molecules and the query pharmacophore model. FIG. 1E shows predicted binding pose of the best hit compound (Chembridge compound 5224046) aligned with the pharmacophore model used for virtual screening. The binding pose recapitulates the pharmacophore model quite well as well as mimicking the hnRNP A1-RNA binding mode (FIG. 1F). To validate the binding predictions, the 154 compounds obtained from commercial sources were screened by NMR in 16-compound batches and 80/154 compounds were found to produce perturbation of hnRNP A18 RRM residues. The majority of "hit" compounds affected a similar set of residues with many of the perturbed residues clustered within a similar location on the RRM. The most significant chemical shift perturbations were obtained with Chembridge 785888 (FIGS. 2A and 2E-2G). FIG. 2B shows a [$^1$H-$^{15}$N] Transverse relaxation optimized spectroscopy-Heteronuclear single quantum coherence spectroscopy (TROSY-HSQC) of the RNA recognition motif domain of hnRNP A18 overlaid with a TROSY-HSQC of hnRNP A18 with Compound 1. The spectra was obtained on a Bruker Avance III 800 MHz spectrometer in 10% $D_2O$ and 5% $d_6$-DMSO in $H_2O$ at 298 K, and concentrations of 150 µM and excess for hnRNP A18 and Chembridge 785888, respectively. While all of the backbone $^{15}$N residues important for RNA binding were significantly perturbed (i.e. F9, R47, F49, F51) in the putative RNA binding pocket, consistent with the inhibitor binding this region, correlations for other backbone resonances were also perturbed and provides evidence that this molecule induces changes in conformation beyond the RNA binding motif of hnRNP A18 (FIGS. 2A and 2E-2G).

EXAMPLE 4

Validation of RNA Binding Inhibition and Specificity

Figure 2C:
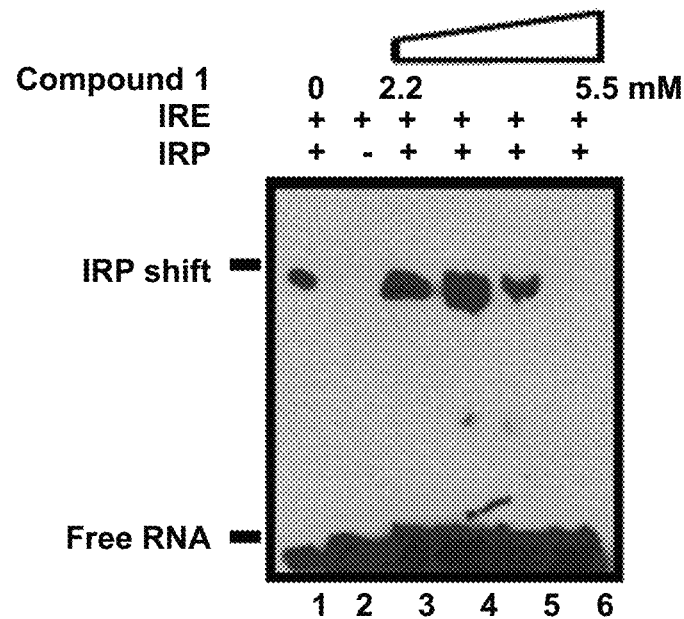
Figure 2D:
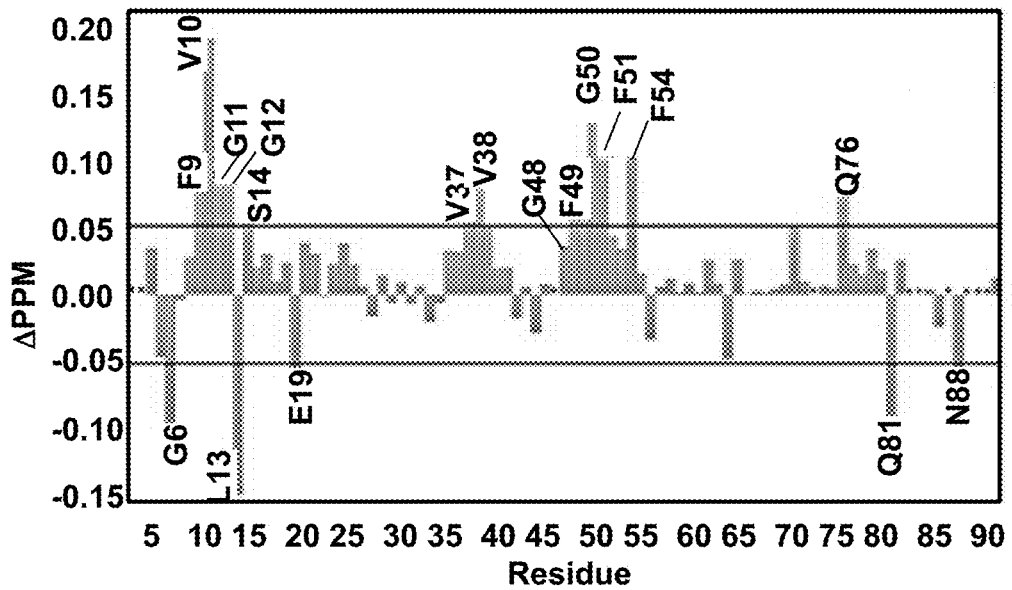
Figure 2E:
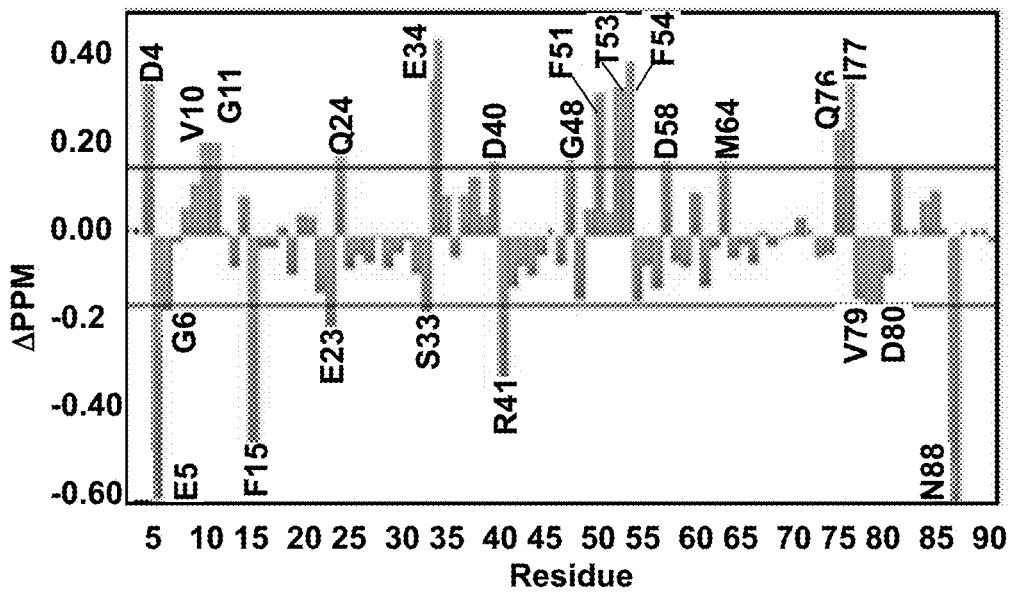
Figure 2F:
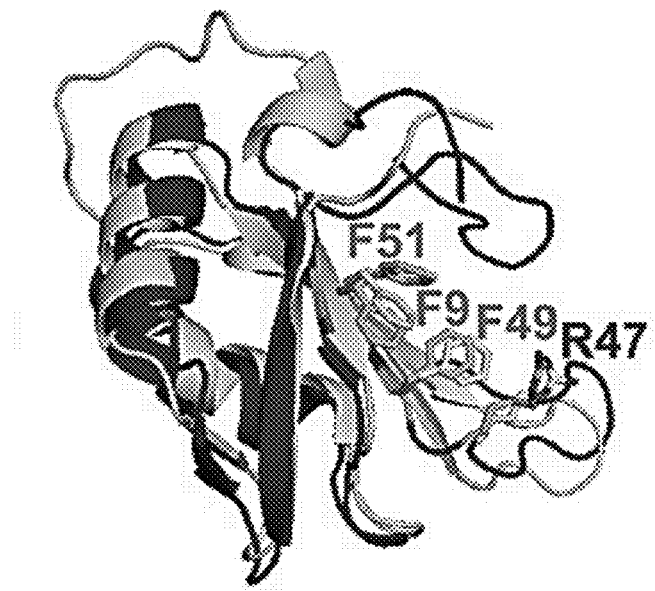
Figure 2G:
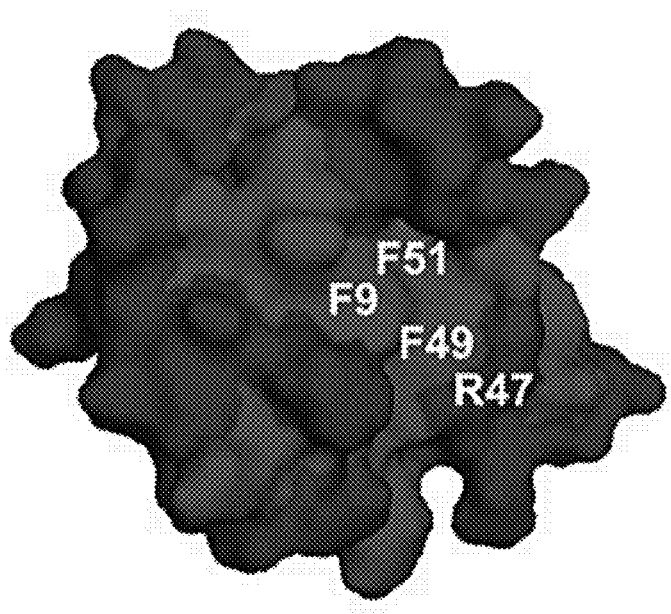
Figure 3A:
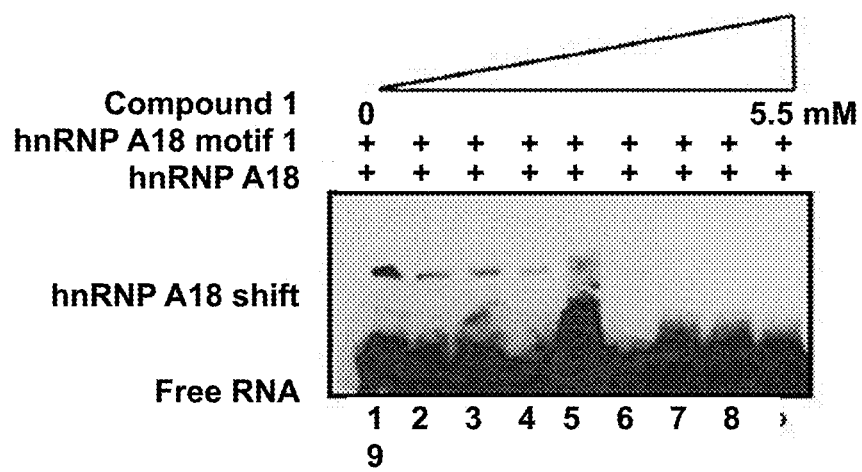
FIGS. 3A-3F shows RNA band shift specificity data.

To determine whether Compound 1 affected hnRNP A18 RNA binding activity, fluorescence anisotropy competition binding experiments were performed. As shown in FIG. 2C, Compound 1 prevented hnRNP A18 from binding to its targeted RNA in a dose-dependent manner with an $IC_{50}$ of 6.4 µM. Subsequent RNA band shift indicated that Compound 1 out-competed hnRNP A18 RNA consensus motif (FIG. 3A) but decreased its specificity at very high concentration (5.5 mM) where binding disruption of an unrelated RNA binding protein, IRP to its targeted RNA (Iron Responsive Element) was also observed (FIG. 2C).

Figure 4A:
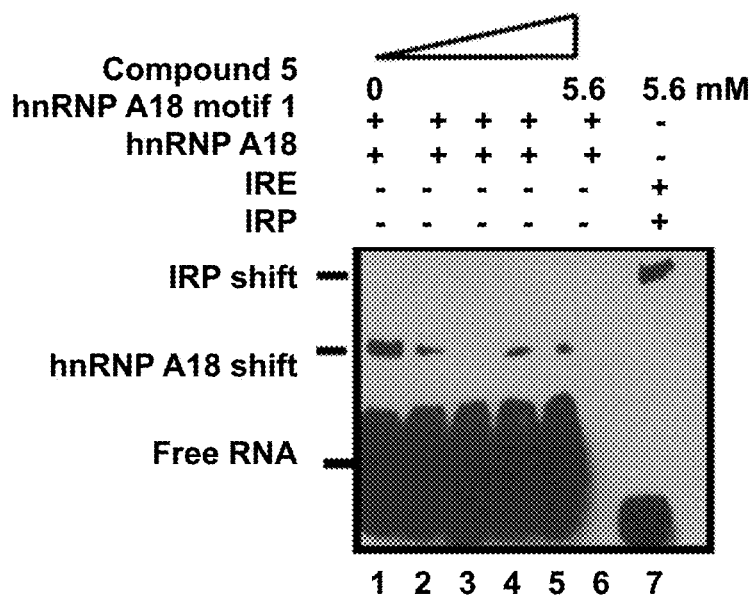
FIGS. 4A-4B shows that Compound 5 specifically disrupt hnRNP A18 RNA binding activity.
Figure 4B:
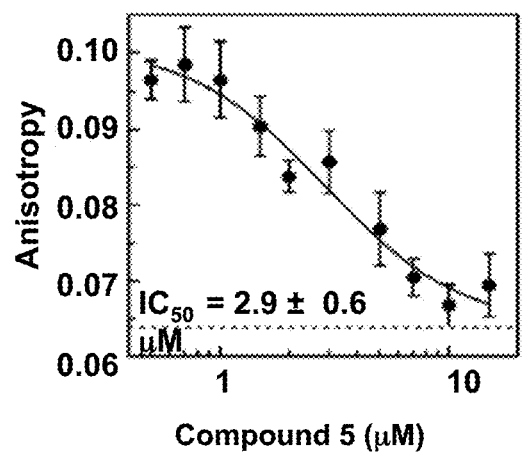
Figure 5A:
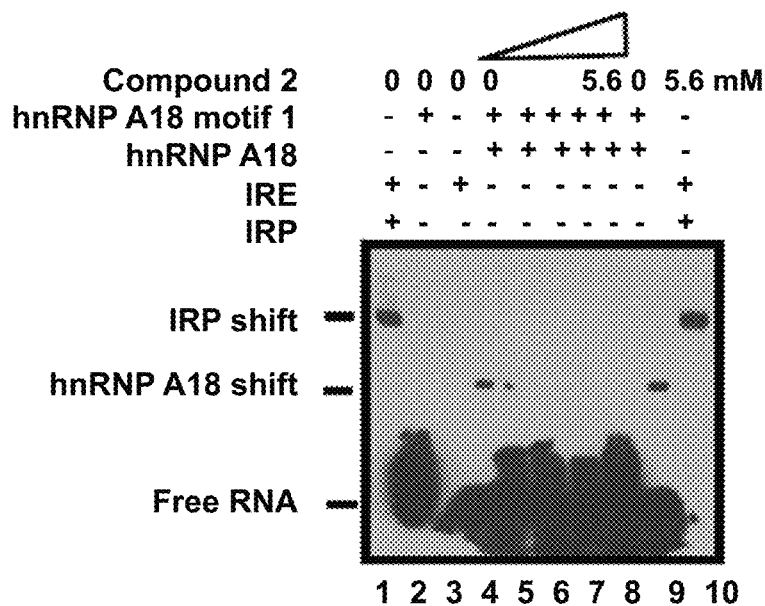
FIGS. 5A-5B shows that Compound 2 specifically disrupt hnRNP A18 RNA binding activity.
Figure 5B:
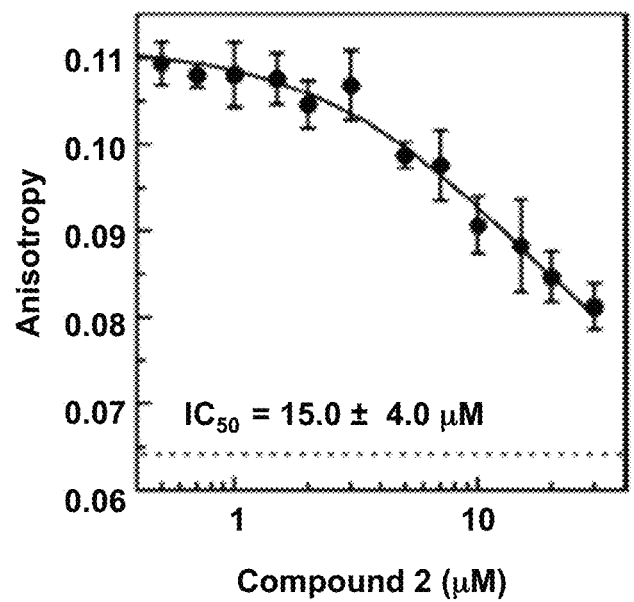
Figure 6A:
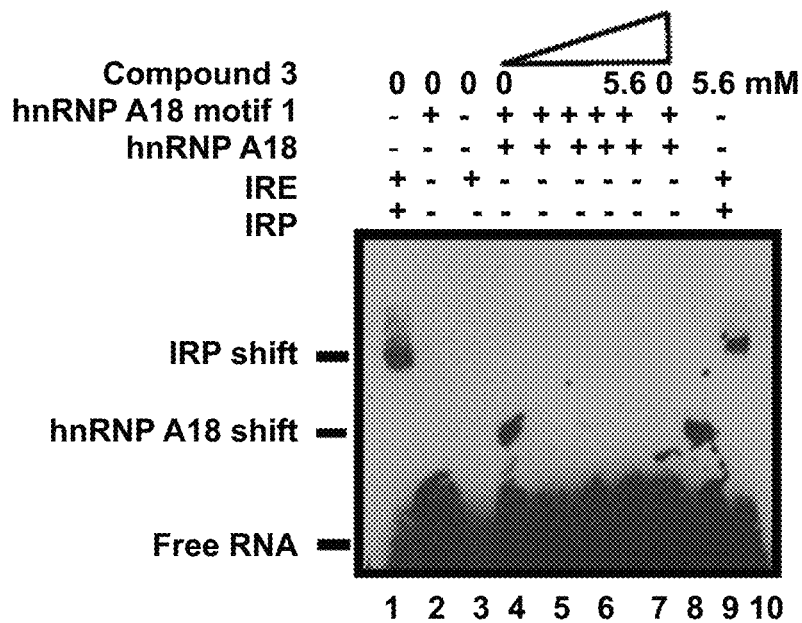
FIGS. 6A-6B shows that Compound 3 specifically disrupt hnRNP A18 RNA binding activity.
Figure 6B:
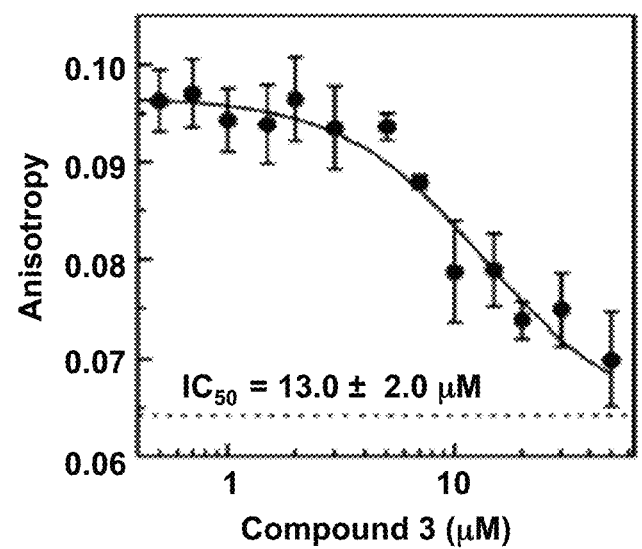
Figure 7A:
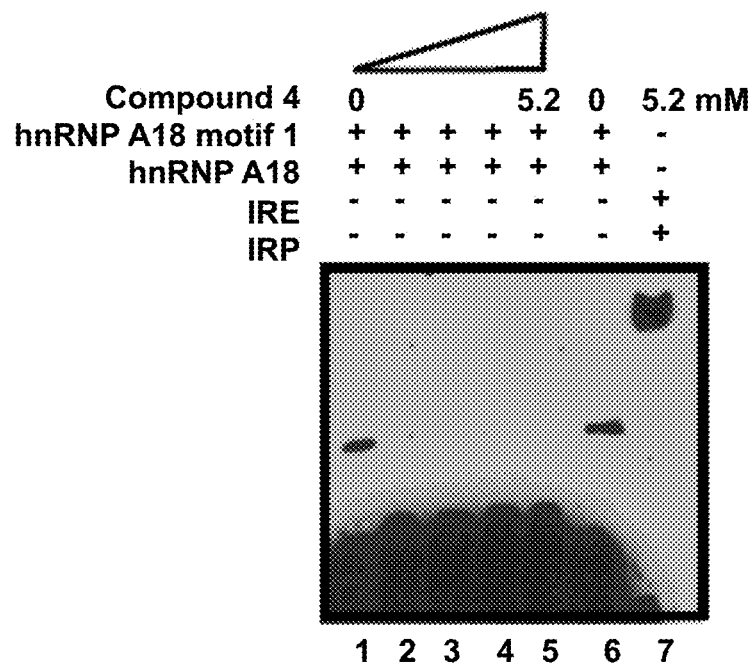
FIGS. 7A-7B shows that Compound 4 specifically disrupt hnRNP A18 RNA binding activity.
Figure 7B:
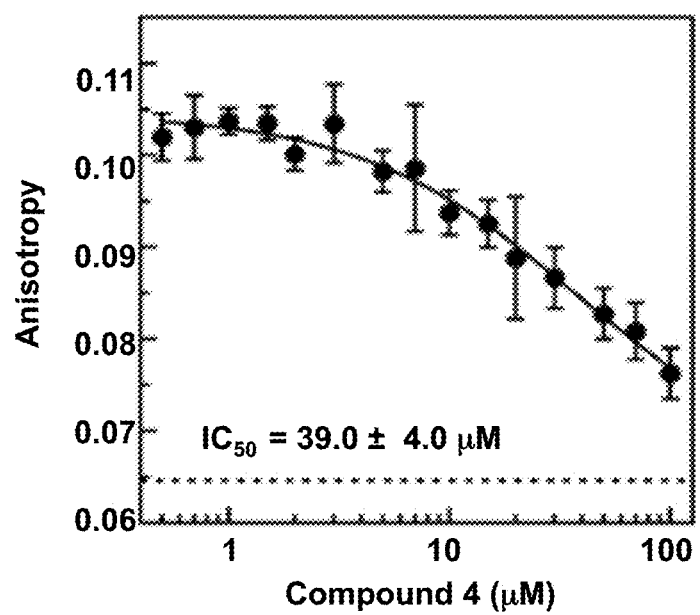
Figure 8A:
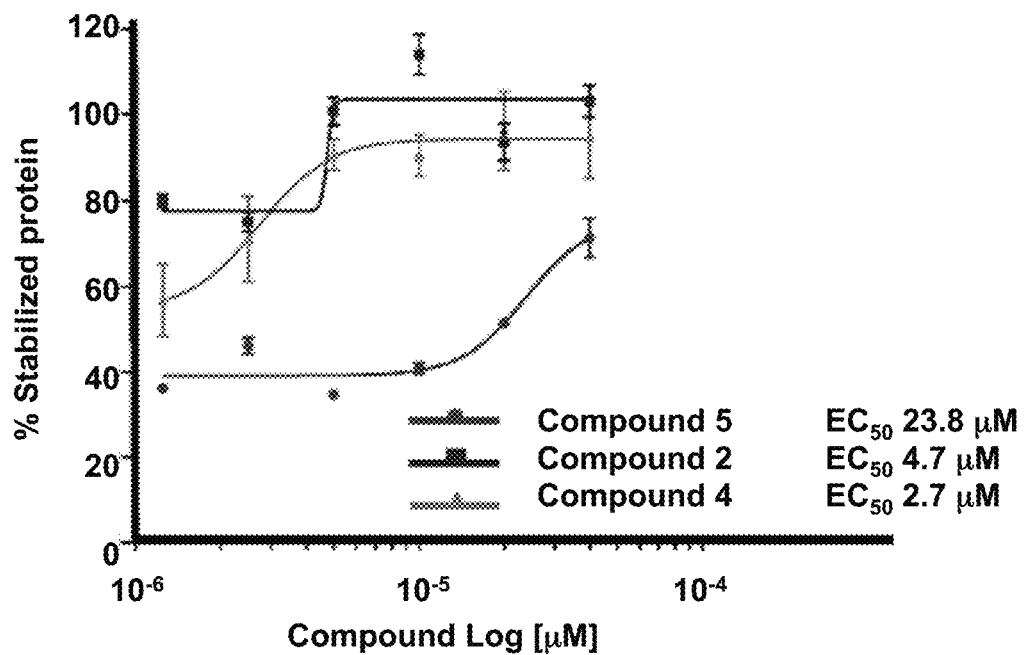
FIGS. 8A-8G demonstrate that the ability of various inhibitors to reach their target, hnRNP A18 in cells and specifically disrupt its RNA binding activity.
Figure 8B:
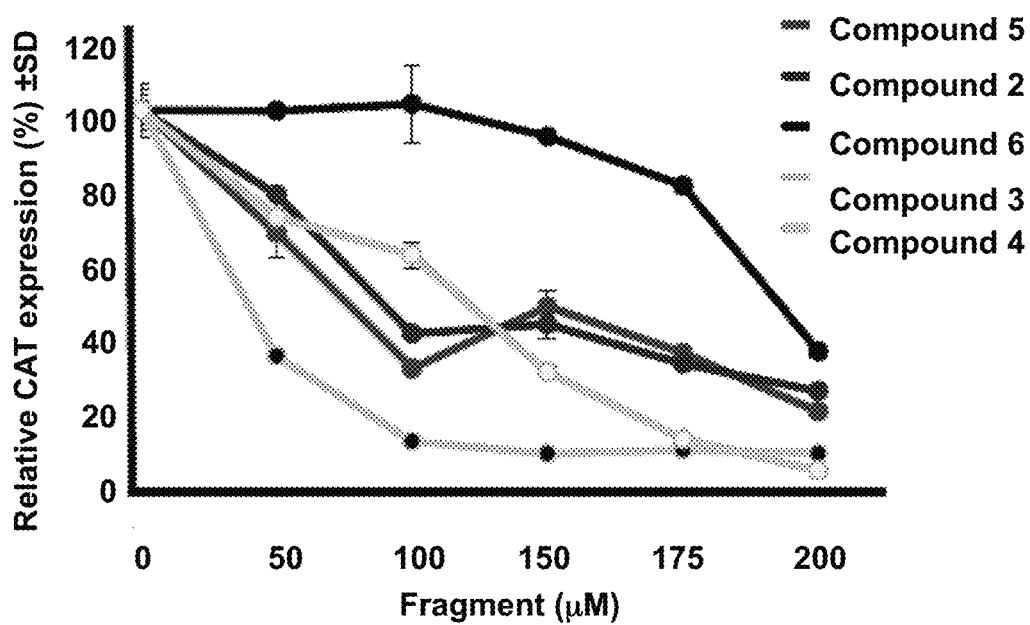
Figure 8C:
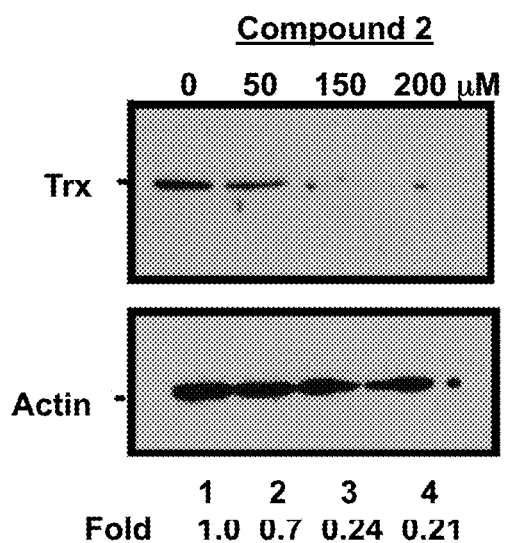
Figure 8D:
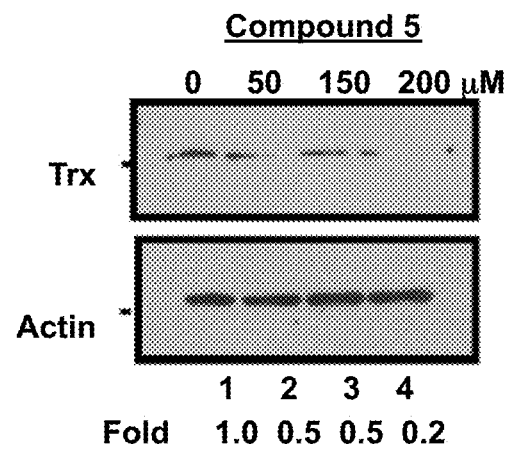
Figure 8E:
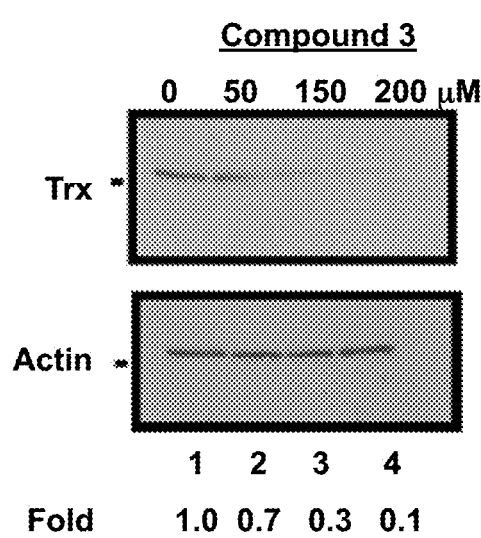
Figure 8F:
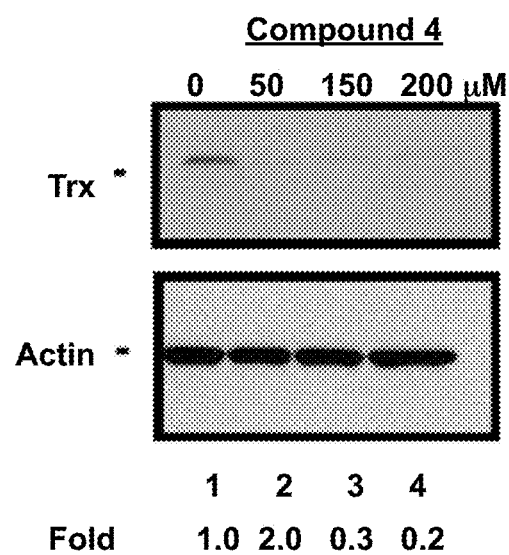
Figure 8G:
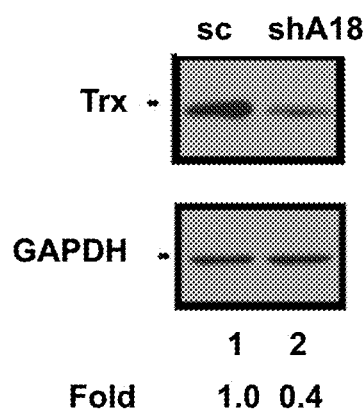

In an effort to bolster specificity, a chemical fingerprint similarity search was performed based on Compound 1 against the UMB CADD center in silico 5.04 million compound database from which 264 compounds were selected. Of these, 81 compounds were selected based on logP and 4DBA (bioavailability) (15) and tested for cell permeability (Parallel artificial membrane permeability assay; PAMPA). Twenty compounds showing higher effective permeability values (Pe>20) were subsequently tested for hnRNP A18 specificity by RNA band shifts. Four compounds, Compound 5 (VITAS STK508411, FIGS. 4A-4B), Compound 2 (Chembridge 7646184, FIGS. 5A-5B), Compound 3 (Chembridge 6823240, FIGS. 6A-6B) and Compound 4 (OTAVA 219853, FIGS. 7A-7B), met the solubility (Pe>20) and RNA binding specificity (no significant IRE competition >5 mM) requirements. Fluorescence anisotropy experiments indicated that the compounds inhibit hnRNP A18 binding to its cognate RNA substrate with $IC_{50}$s of 2.9, 15, 13 and 39 µM respectively (FIGS. 4B, 5B, 6B, and 7B).

To verify that these compounds can reach their target (hnRNP A18) in cells, a Cellular Engagement Thermal Shift Assay (CETSA) was performed on three of these compounds in human melanoma cells. The data shown in FIG. 8A indicate that Compound 5, Compound 2 and Compound 4 can bind to and stabilize hnRNP A18 in human cells with $EC_{50}$s of 23.8, 4.7 and 2.7 µM respectively.

Figure 3B:
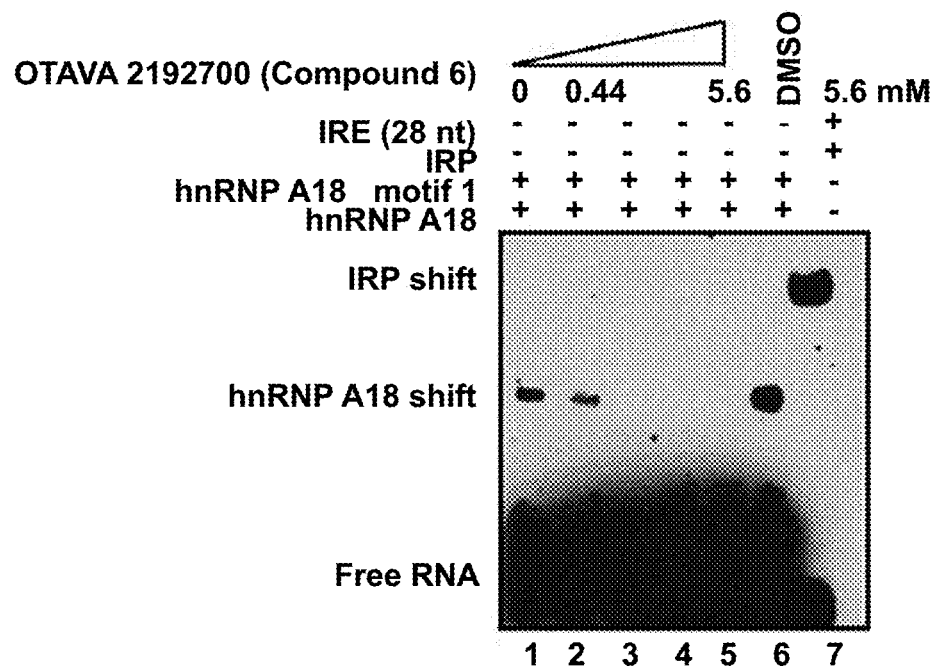
Figure 3C:
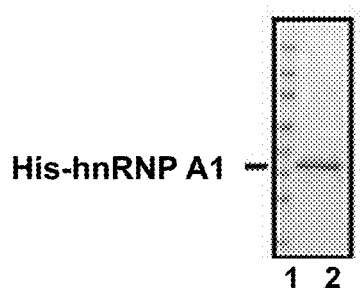
Figure 3D:
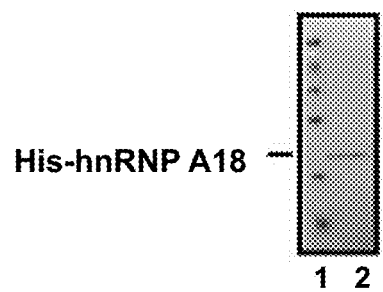
Figure 3E:
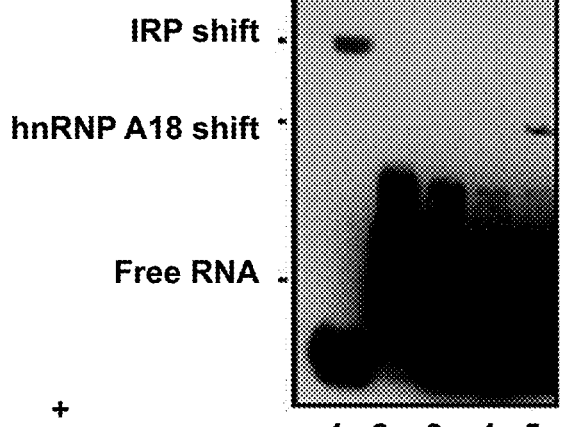
Figure 3F:
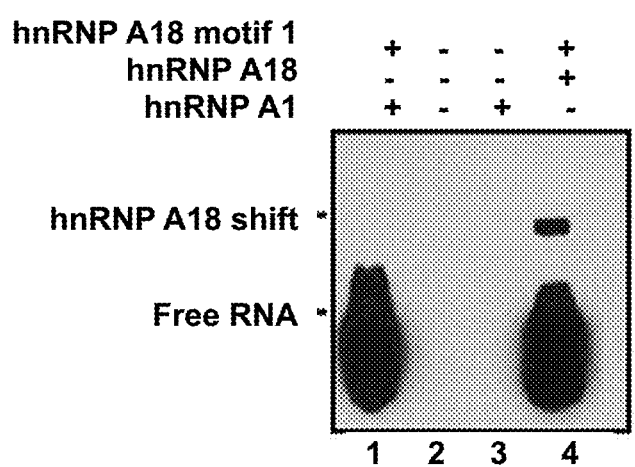

In order to determine whether hnRNP A18 binding to these compounds disrupted its cellular functions, a cell-based assay was developed as a read out for hnRNP A18 RNA binding activity. A reporter vector harboring a hnRNP A18 targeted 3'UTR (Trx; (16)) downstream of a CAT gene was engineered. Binding of hnRNP A18 to the targeted 3'UTR is expected to stabilize the CAT transcript and increase CAT protein production, which is then measured by ELISA. The data (FIG. 8B) indicate that the four compounds that competed hnRNP A18 RNA binding activity in vitro (FIGS. 3A-3F) also reduced the production of the CAT protein suggesting that indeed the compounds disrupted hnRNP A18 binding to its targeted transcripts in cells. In contrast, Compound 6 (OTAVA 2192700), which specifically competed for hnRNP A18 binding activity by band shift (FIG. 3B), could only reduce CAT protein levels at the highest concentration. Low aqueous solubility of Compound 6 likely accounts for its relatively reduced activity in cells.

To verify that the four active compounds affected the production of the targeted transcripts in cells, Western blot analysis was performed following exposure of melanoma LOX IM VI cells to these compounds. FIGS. 8C and 8E-8G indicate that indeed all four compounds disrupted Thioredoxin protein level in a dose dependent manner to levels similar to what was achieved with shRNA hnRNP A18 (FIG. 8D, (5)).

The data indicates that the hnRNP A18 RNA recognition motif is also located in the 3'UTR of the immune checkpoint transcript CTLA-4 (FIG. 9A). The motif has about 80% similarity (41/51 nucleotides) to the consensus recognition motifs as well as five of the six invariant nucleotides having SEQ ID NOS: 9-14 (boxed, FIG. 9A). The Trx transcript (SEQ ID NO: 15) and CTLA-4 transcript (SEQ ID NO: 16) are shown. Unmatched nucleotides in the CTLA-4 transcript are shown in lowercase italics. The position of the motif relative to the 3'-UTR start site is indicated in parentheses.

Figure 9E:
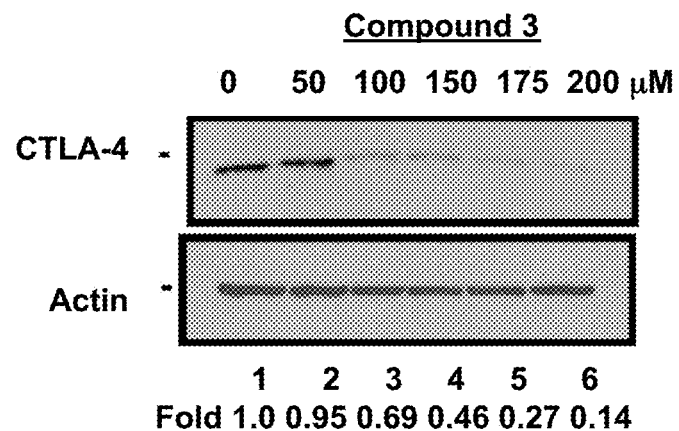
Figure 9F:
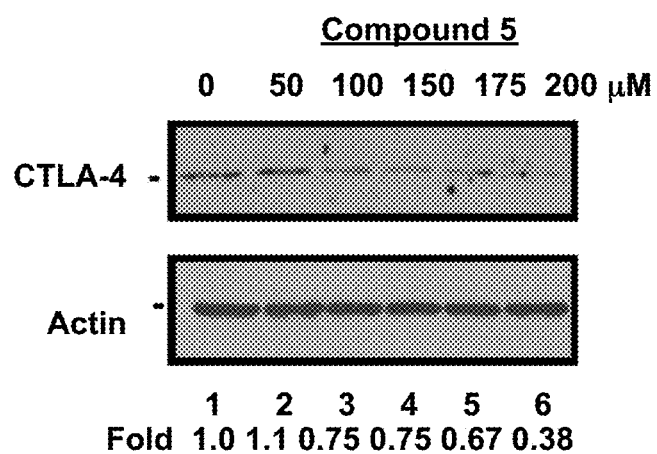
Figure 9G:
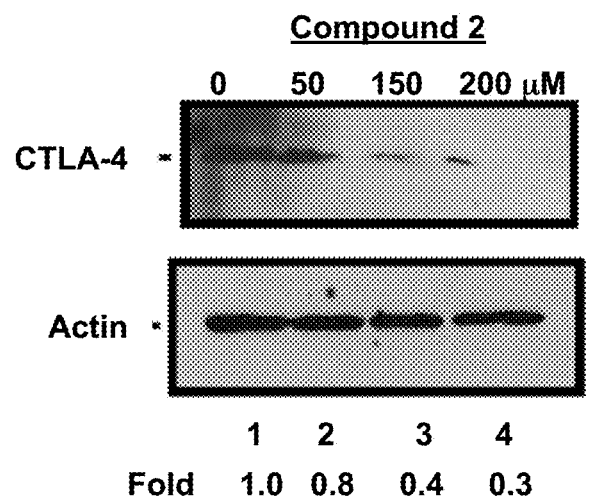
Figure 9H:
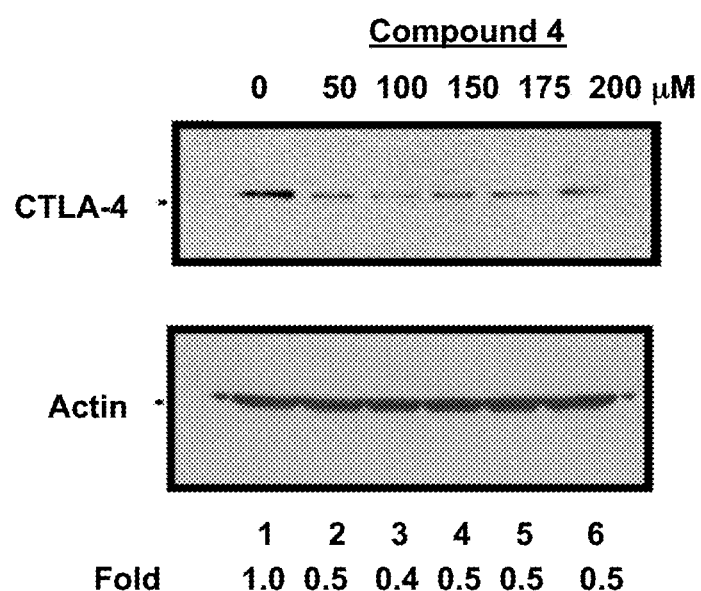

To validate the hnRNP A18 recognition motif in CTLA-4 transcript a RNA-IP was performed in human prostate cancer PC-3 cells. The RNA IP was performed as described (11, 16) under conditions that preserve RNA-protein interaction on polysomes. Data shown in FIG. 9B indicate that indeed hnRNP A18 can bind to CTLA-4 transcript on polysomes. Moreover, in a PC-3 tumor mouse model the tumor expressing the highest levels of hnRNP A18 also expressed the highest levels of CTLA-4 (tumor #1, FIG. 9D) and was the most aggressive (FIG. 9C) while the tumor expressing the lowest level of hnRNP A18 (tumor # 2, FIG. 9D) had reduced CTLA-4 protein level and was less aggressive (FIG. 9C). Although the level of CTLA-4 could not account for the aggressiveness of the tumor in this immunocompromised xenograft mouse model, it suggests that hnRNP A18 could contribute to tumor immune evasion in immunocompetent systems. Most importantly, the protein translation inhibitors targeting hnRNP A18 decreased CTLA-4 expression in PC-3, LOX-IM-VI and MiaPaca cells in a dose dependent manner (FIGS. 9E-9H). These protein translation inhibitors thus do not disrupt hnRNP A18 protein levels (FIG. 8A) but rather prevent its binding to targeted transcripts (FIGS. 4A-4B, FIGS. 5A-5B, FIGS. 6A-6B, and FIGS. 7A-7B) and reduce levels of their encoded proteins (FIGS. 8C, 8E-8G and FIGS. 9E-9H).

Figure 10A:
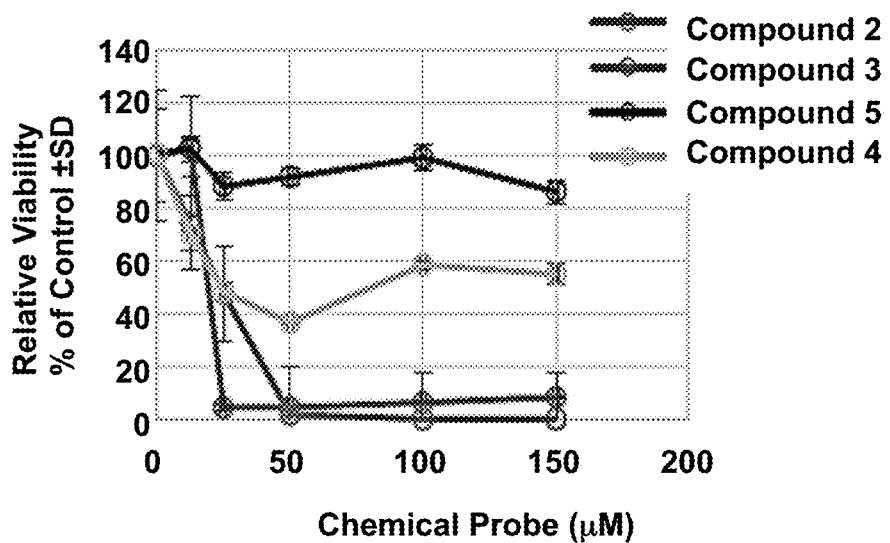
FIGS. 10A-10F shows that cytotoxicity to the inhibitor compounds is selective for human cancer cells.
Figure 10B:
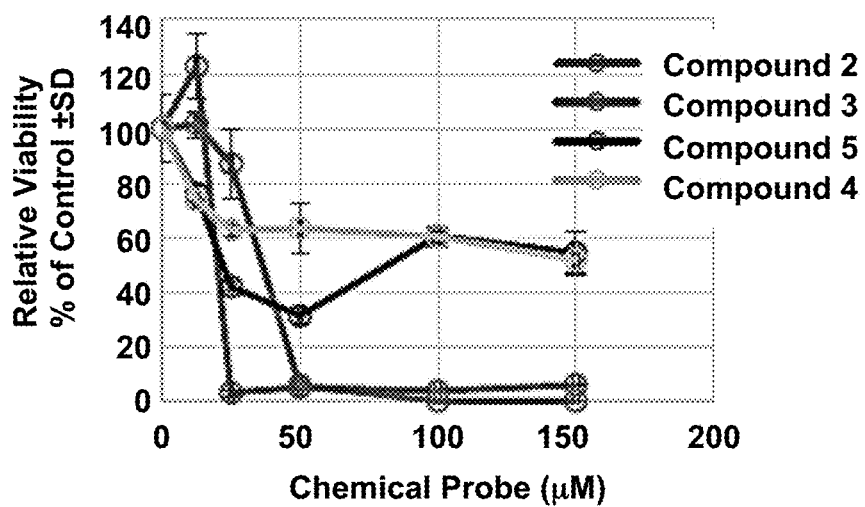
Figure 10C:
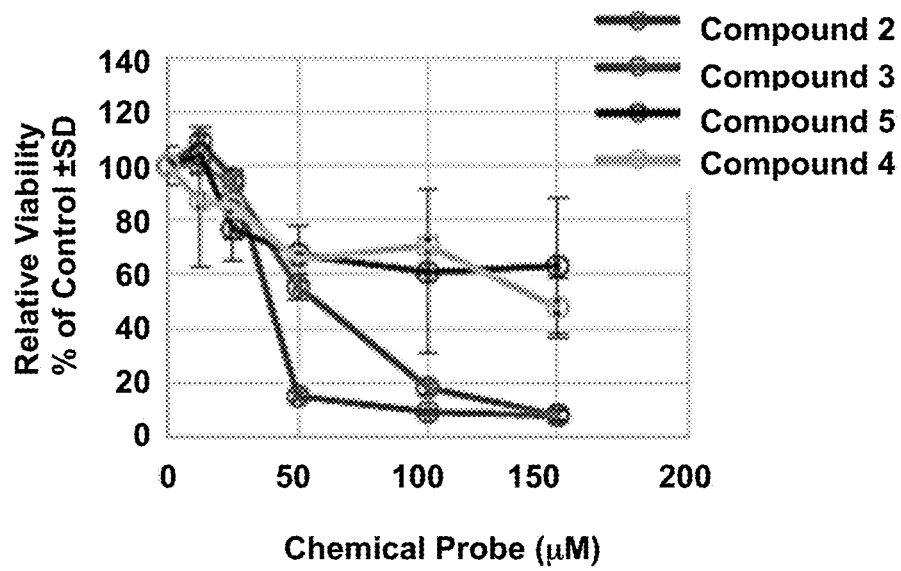
Figure 10D:
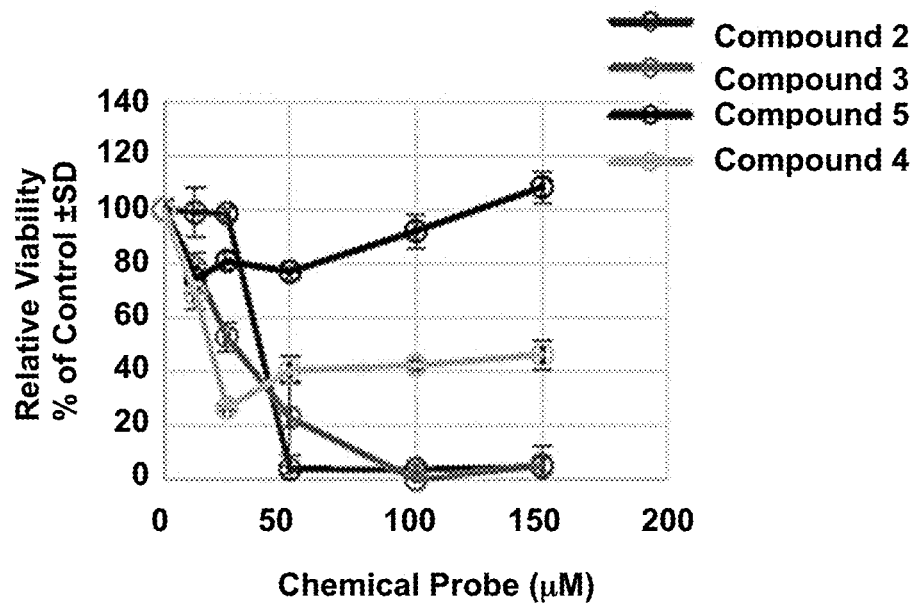
Figure 10E:
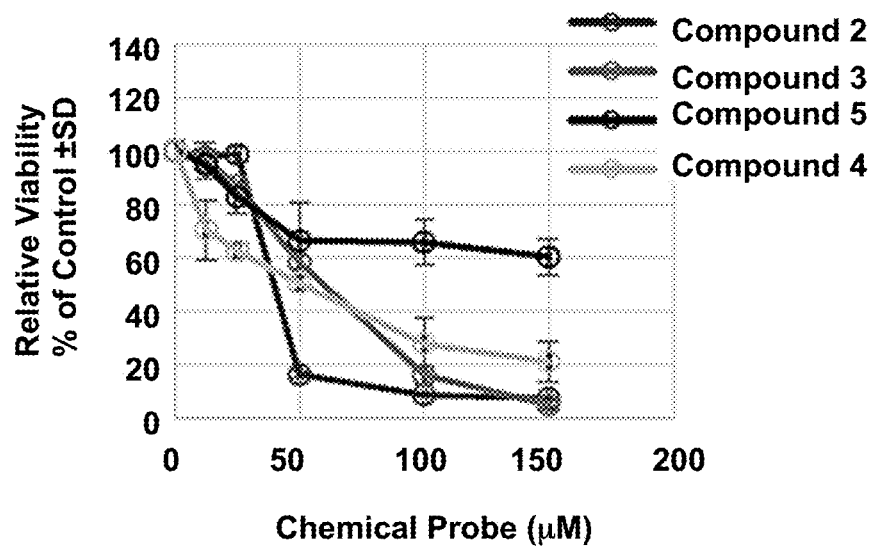
Figure 10F:
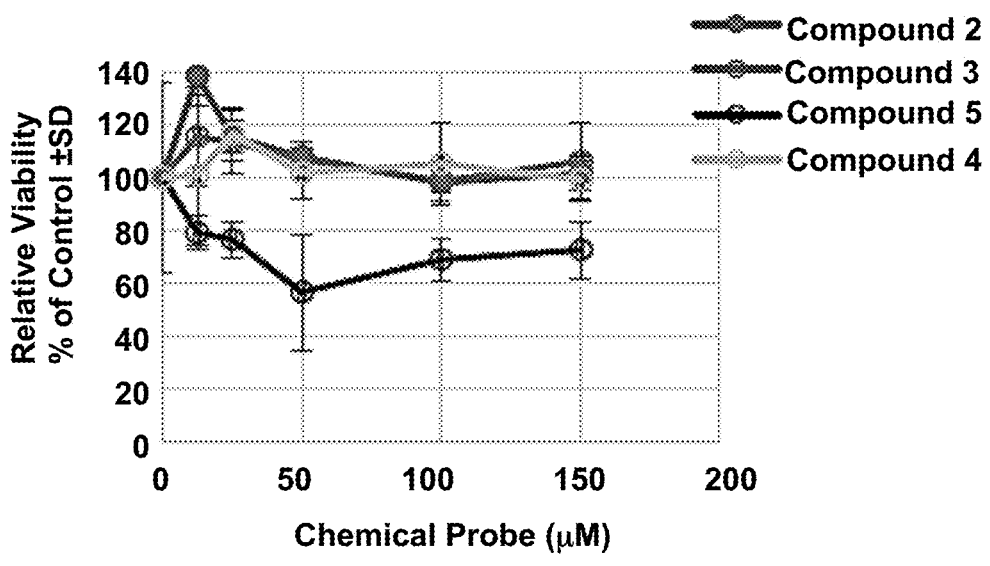

Next, the potential therapeutic index of these compounds was evaluated by measuring their effects on normal and cancer cells viability. Data shown in FIGS. 10A-10E indicate that protein translation inhibitors Compound 2 and Compound 3 were the most effective, killing all cancer cell lines tested without affecting the viability of normal human epithelial cells even at doses as high as 150 µM (FIG. 10F). Compound 4 also had no significant effect on normal cells viability (FIG. 10F), while preferentially killing cancer cells although less efficiently than Compounds 2 and 3. Compound 5 was the least effective with some degree (20-40%) of toxicity to normal cells. These data thus suggest that the protein translation inhibitors identified here could contribute to elucidate the underexplored biological function of RNA-Binding Proteins in cancer cells proliferation and serve as valuable scaffolds for development of improved small molecules with a desirable therapeutic index.

The following references are cited herein:
1. Scheper et al. (2007) Nat Rev Genet 8(9):711-723.
2. Cam H & Houghton P J (2011) Target Oncol 6(2):95-102.
3. Pamboukian et al. (2012) Molecular and Cellular Pharmacology 4(1):41-48.
4. Pereira et al. (2017) Trends Cancer 3(7):506-528.
5. Chang et al. (2016) Oncotarget 7(9):10578-10593.
6. Fornace et al. (1988) Proc Natl Acad Sci USA 85(23): 8800-8804.
7. Sheikh et al. (1997) J Biol Chem 272 (42):26720-26726.
8 Nishiyama et al. (1997) J Cell Biol 137(4):899-908.
9. Yang C & Carrier F (2001) J Biol Chem 276(50):47277-47284.
10. Wellmann et al. (2004) J Cell Sci 117(Pt 9):1785-1794.
11. Yang R et al. (2010) J Biol Chem 285(12):8887-8893.
12. Coburn et al. (2017) Acta Crystallogr F Struct Biol Commun 73(Pt 4):209-214.
13. Guvench O & MacKerell A D, Jr. (2009) PLoS Comput Biol 5(7):e1000435.
14. Raman et al. (2013) J Chem Inf Model 53(12):3384-3398.
15. Oashi et al. (2011) J Chem Inf Model 51(1):148-158.
16. Yang et al. (2006) Nucleic Acids Res 34(4):1224-1236.
17. Thomas J R & Hergenrother P J (2008) Chem Rev 108(4):1171-1224.
18. Hanahan D & Weinberg R A (2011) Cell 144(5):646-674.
19. Novotny et al. (2016) Neoplasma 63(4):495-503.
20. Showkat et al. (2014) Mol Biol Int 2014:686984.
21. Langdon et al. (2018) et al. Oncoimmunology 7(8): e1458810.
22. Schneider H et al. (2014) Front Immunol. 5(619):1-10.
23. Raman et al. (2011) et al. J Chem Inf Model 51(4):877-896.
24. Lakkaraju et al. (2014) et al. J Chem Theory Comput 10(6):2281-2290.
25. Yu et al. (2015) et al. J Chem Inf Model 55(2):407-420.
26. Word et al. (1999) et al. J Mol Biol 285(4):1735-1747.
27. Van Der Spoel et al. (2005) et al. J Comput Chem 26(16):1701-1718.
28. Best et al. (2012) J Chem Theory Comput 8(9):3257-3273.
29. MacKerell et al. (1998) et al. J Phys Chem B 102(18): 3586-3616.
30. Vanommesiaeghe et al. (2010) et al. J Comput Chem 31(4):671-690.
31. Yu et al. (2012) et al. J Comput Chem 33(31):2451-2468.
32. Jorgensen et al. (1983) et al. J. Chem. Phys. 79:926-935.
33. Koes D R & Camacho C J (2011) J Chem Inf Model 51(6):1307-1314.
34. Kansy et al. (1998) et al. J Med Chem 41(7):1007-1010.
35. Delaglio et al. (1995) et al. J Biomol NMR 6(3):277-293.
36. Zucconi B E & Wilson G M (2013) et al. J Bio Chem 288(39):28034-28048.

What is claimed is:

1. A protein translation inhibitor, comprising:
a compound that binds to an RNA Recognition motif in a heterogenous ribonucleoprotein A18 with a chemical structure:

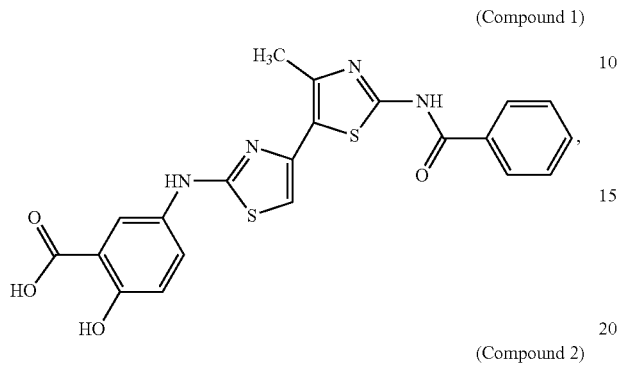
(Compound 1)

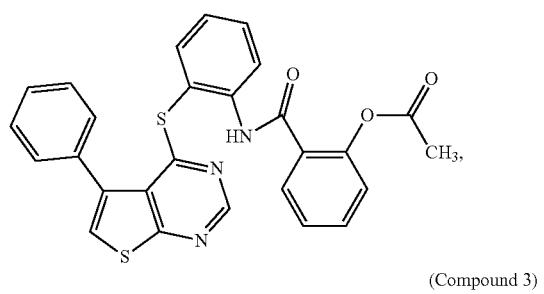
(Compound 2)

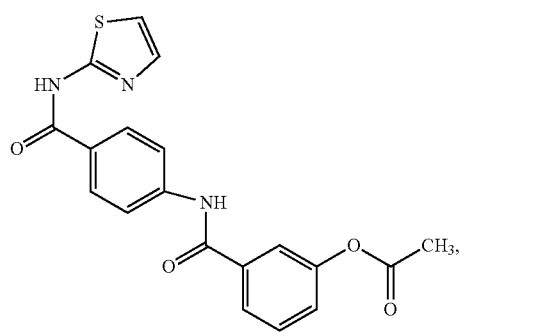
(Compound 3)

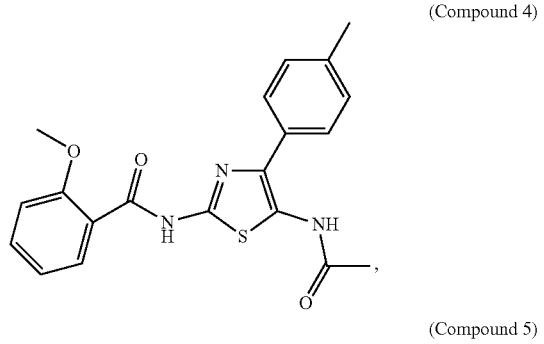
(Compound 4)

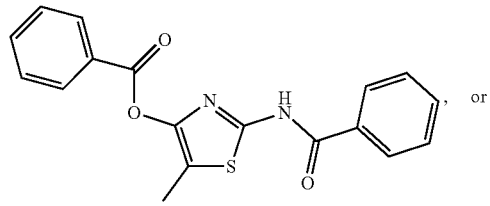
(Compound 5), or

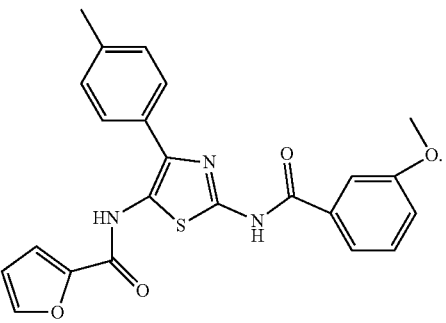
(Compound 6)

2. The protein translation inhibitor of claim 1, wherein the compound inhibits binding of the heterogenous ribonucleoprotein A18 to an mRNA transcript for a protein associated with cancer cell proliferation.

3. The protein translation inhibitor of claim 2, wherein the protein associated with cancer cell proliferation is thioredoxin, vascular endothelial growth factor, or replication protein A or a combination thereof.

4. The protein translation inhibitor of claim 1, wherein the compound inhibits binding of the heterogenous ribonucleoprotein A18 to an mRNA transcript for a tumor immune checkpoint protein.

5. The protein translation inhibitor of claim 4, wherein the tumor immune checkpoint protein is cytotoxic T-lymphocyte-associated protein 4, programmed cell death protein 1, programmed death-ligand 1, or a combination thereof.

6. A pharmaceutical composition comprising the protein translation inhibitor of claim 1 and a pharmaceutically acceptable carrier.

7. A method for treating a cancer in a subject in need thereof comprising the step of:
administering to the subject a therapeutically effective amount of the protein translation inhibitor of claim 1, thereby inhibiting translation of a protein associated with the cancer.

8. The method of claim 7, wherein the protein translation inhibitor is

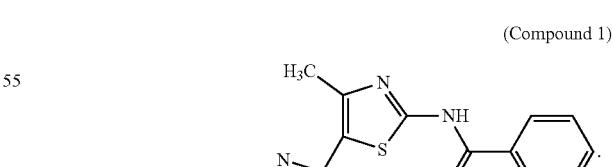
(Compound 1)

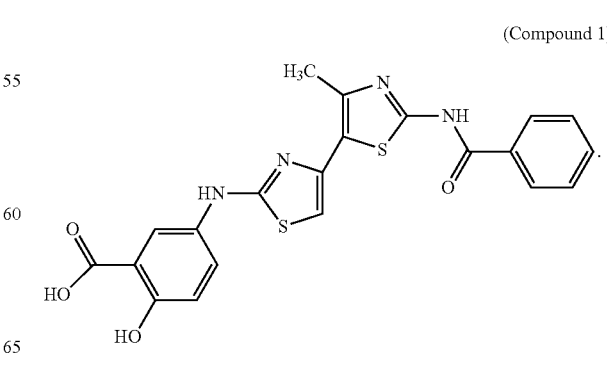

9. The method of claim 7, wherein the protein translation inhibitor is (Compound 2)

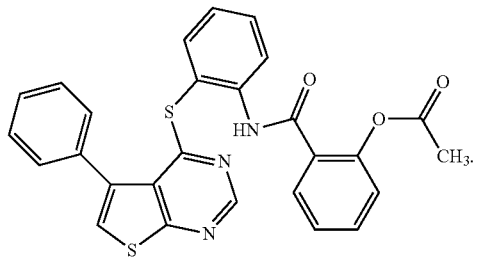

10. The method of claim 7, wherein the protein translation inhibitor is (Compound 3)

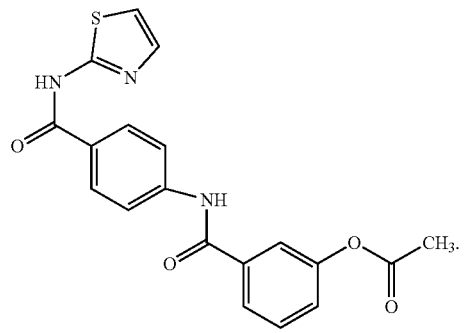

11. The method of claim 7, wherein the protein translation inhibitor is (Compound 4)

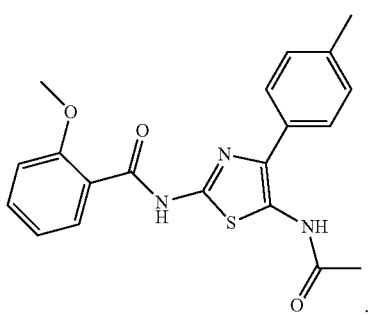

12. The method of claim 7, wherein the protein translation inhibitor is (Compound 5)

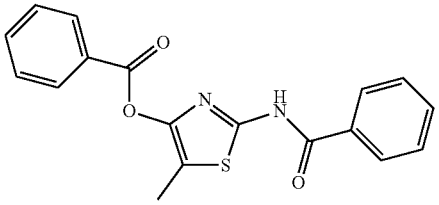

13. The method of claim 7, wherein the protein translation inhibitor is (Compound 6)

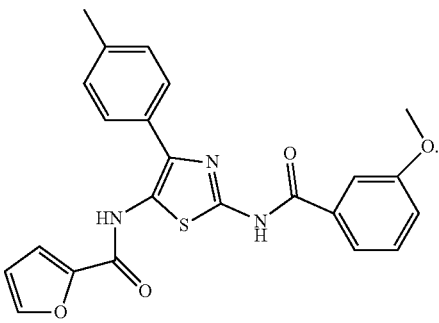

14. The method of claim 7, wherein the cancer is a melanoma, a lung cancer, a prostate cancer, an intestinal cancer, a colon cancer, a pancreatic cancer, a gall bladder cancer, a bile duct cancer, a brain cancer, a glioblastoma, a breast cancer, a hepatocellular carcinoma, a kidney cancer, a bladder cancer, or a lymphoma.

* * * * *